(12) United States Patent
Lohse

(10) Patent No.: US 8,546,309 B2
(45) Date of Patent: Oct. 1, 2013

(54) MONOMERIC AND POLYMERIC LINKERS USEFUL FOR CONJUGATING BIOLOGICAL MOLECULES AND OTHER SUBSTANCES

(75) Inventor: Jesper Lohse, København NV (DK)

(73) Assignee: Dako Denmark A/S, Glostrupk (DK)

( * ) Notice: Subject to any disclaimer, the term of this patent is extended or adjusted under 35 U.S.C. 154(b) by 982 days.

(21) Appl. No.: 11/993,545

(22) PCT Filed: Jun. 30, 2006

(86) PCT No.: PCT/IB2006/002584
§ 371 (c)(1),
(2), (4) Date: Jan. 4, 2010

(87) PCT Pub. No.: WO2007/015168
PCT Pub. Date: Feb. 8, 2007

(65) Prior Publication Data
US 2010/0120054 A1    May 13, 2010

Related U.S. Application Data

(60) Provisional application No. 60/695,408, filed on Jul. 1, 2005, provisional application No. 60/695,409, filed on Jul. 1, 2005, provisional application No. 60/695,410, filed on Jul. 1, 2005.

(51) Int. Cl.
*C40B 80/00* (2006.01)
*C12Q 1/70* (2006.01)
*C12Q 1/68* (2006.01)
*G01N 33/53* (2006.01)
*C07H 21/02* (2006.01)
*C07H 19/04* (2006.01)

(52) U.S. Cl.
USPC ............... 506/42; 435/5; 435/6.1; 435/7.1; 435/7.2; 536/23.1; 536/26.6

(58) Field of Classification Search
USPC .............. 435/5, 6.1, 7.1, 7.2; 536/23.1, 26.6; 506/42
See application file for complete search history.

(56) References Cited

U.S. PATENT DOCUMENTS 4,447,574 A    5/1984  Keske et al.
5,723,591 A    3/1998  Livak et al.

FOREIGN PATENT DOCUMENTS

WO    WO99/43780          9/1999
WO    WO02/063299         8/2002
WO    WO2004/091542 A2   10/2004

OTHER PUBLICATIONS

Landis, "Solid Phase synthesis of chiral 3,4-diazaphospholanes and their application to catalytic asymmetric allylic alkylation", Proceedings of the National Academy of Sciences of USA, National Academy of Science, Washington DC, Apr. 13, 2004, pp. 5428-5432, vol. 101, No. 15.

(Continued)

*Primary Examiner* — Jezia Riley
(74) *Attorney, Agent, or Firm* — Finnegan, Henderson, Farabow, Garrett & Dunner L.L.P.

(57) ABSTRACT

The present invention concerns monomeric or polymeric linker molecules useful in biological and chemical applications, their synthesis, and the synthesis and use of derivatives of the linkers conjugated to a variety of detectable labels and other substances. The linkers may be used, for example, in conjunction with fluorescent labels, nucleic acid or nucleic acid analog probes, and solid phase systems, and to enhance the solubility of the conjugated molecules.

19 Claims, 13 Drawing Sheets

(56) References Cited

OTHER PUBLICATIONS

Suzuki, "Design and Synthesis of Calcium and Magnesium Ionophores Based on Double-Armed Diazacrown Ether Compounds and Their Application to an Ion-Sensing Component for an Ion-Selective Electrode", Analytical Chemistry, 1995., pp. 324-334, No. 67.

Greenwald, "A New Aliphatic Amino Prodrug System for the Delivery of Small Molecules and Proteins Utilizing Novel PEG Derivatives", J. Med. Chem., 2004, pp. 726-734, vol. 47.

Krishnan et al., "Synthesis, characterization and kinetic study of hydrolysis of polyamic acid derived from ODPA and $m$-tolidine and related compounds", Polymer, 2001, pp. 5165-5174, vol. 42.

Lozinskaya et al., "Direct Polycondensation in ionic liquids", European Polymer Journal, 2004, pp. 2065-2075, vol. 40.

Linker derivative with conjugated antibody
and
fluorophores recognizing a target antigen.

Linker derivative with nucleic acid or nucleic
acid analog and fluorophore conjugates
recognizing a target nucleic acid.

Exemplary multi-layer assay system

Figure 5

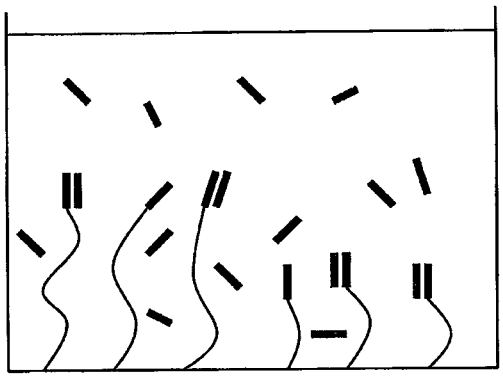

Figure 5A: Capture slow relative to diffusion

Concentration of target remains largely constant due to fast diffusion. The linker length of the probes are of less importance.

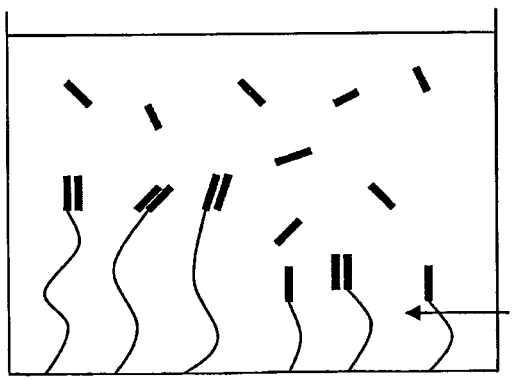

Figure 5B: Capture fast relative to diffusion

Depleted capture zone. Diffusion of target will limit capture, and probes on longer linkers capture more efficiently because they capture in larger volume.

Figure 6
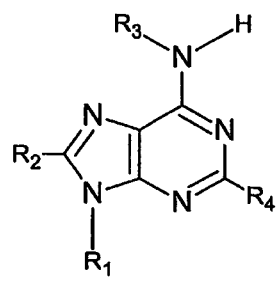
Figure 6a, Adenine, A
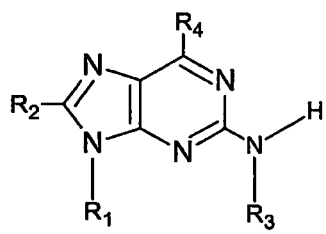
Figure 6b, isoAdenine, isoA
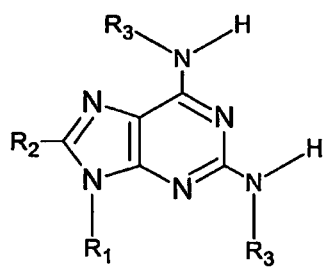
Figure 6c, Diaminopurine, D
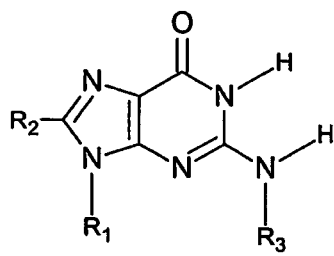
Figure 6d, Guanine, G

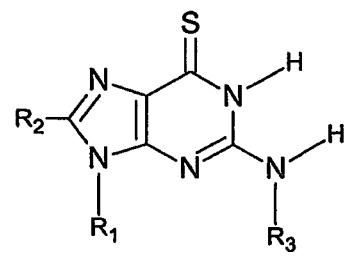
Figure 6e, ThioGuanine, Gs
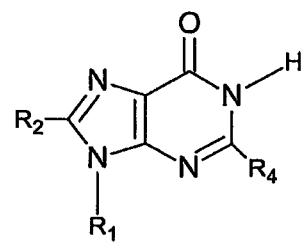
Figure 6f, Inosine, I
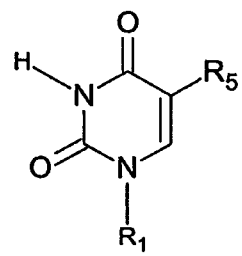
Figure 6g, Uracil, U
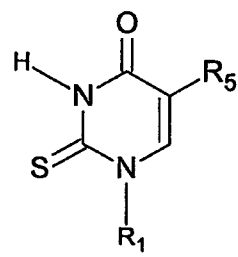
Figure 6h, 2-ThioUracil, U2s

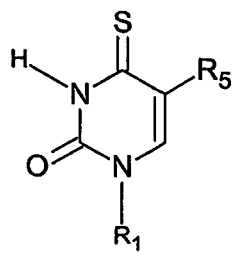
Figure 6i, 4-ThioUracil, U4s
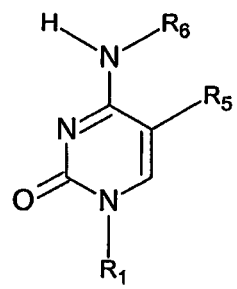
Figure 6j, Cytosine, C
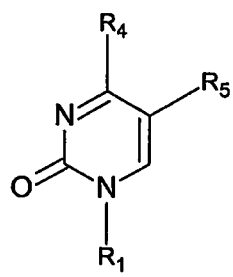
Figure 6k, 2-oxo-Pyrimidine, Py-2o
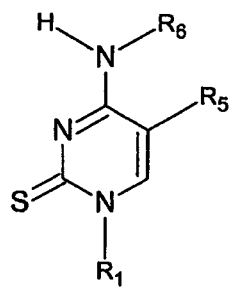
Figure 6l, ThioCytosine, Cs

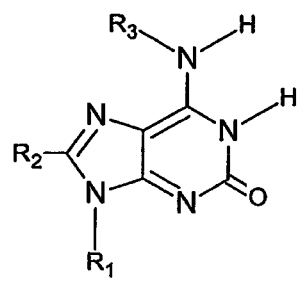
Figure 6m, isoGuanine, isoG
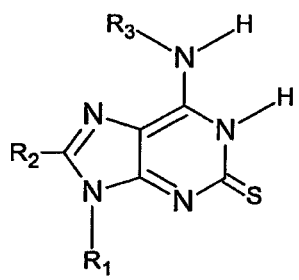
Figure 6n, isothioGuanine, isoGs
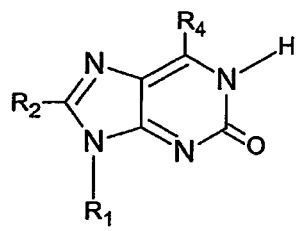
Figure 6o, 2-oxoPurine, Pu-2o
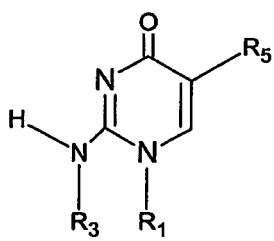
Figure 6p, isoCytosine, isoC

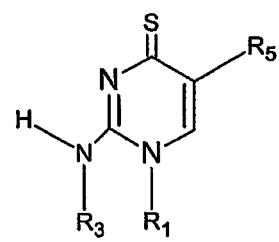
Figure 6q, isothioCytosine, isoCs
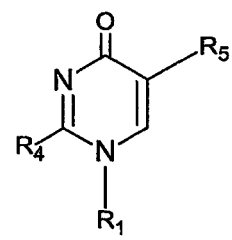
Figure 6r, 4-oxoPyrimidine, Py-4o

SEQUENCE LISTING

```
<160> NUMBER OF SEQ ID NOS: 11

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 1
tgtaccttga                                                             10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 2
aacgggataa ctgcacct                                                    18

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)..(4)
<223> OTHER INFORMATION: Diaminopurine
<220> FEATURE:
<221> NAME/KEY: modified_base
<222> LOCATION: (5)..(6)
<223> OTHER INFORMATION: Thioguanine

<400> SEQUENCE: 3 tcnnnntaca                                                             10

<210> SEQ ID NO 4
<211> LENGTH: 10
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: 2/4-thiouracil
<220> FEATURE:
<221> NAME/KEY: modified_base
<222> LOCATION: (3)
<223> OTHER INFORMATION: 2/4-thiouracil
<220> FEATURE:
<221> NAME/KEY: modified_base
```

```
<222> LOCATION: (4)
<223> OTHER INFORMATION: Diaminopurine
<220> FEATURE:
<221> NAME/KEY: modified_base
<222> LOCATION: (5)..(6)
<223> OTHER INFORMATION: Pyrimidone
<220> FEATURE:
<221> NAME/KEY: modified_base
<222> LOCATION: (10)
<223> OTHER INFORMATION: Diaminopurine

<400> SEQUENCE: 4 ngnnnnttgn                                                                  10

<210> SEQ ID NO 5
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (2)
<223> OTHER INFORMATION: 2/4-thiouracil
<220> FEATURE:
<221> NAME/KEY: modified_base
<222> LOCATION: (3)..(4)
<223> OTHER INFORMATION: Thioguanine
<220> FEATURE:
<221> NAME/KEY: modified_base
<222> LOCATION: (5)..(6)
<223> OTHER INFORMATION: Diaminopurine
<220> FEATURE:
<221> NAME/KEY: modified_base
<222> LOCATION: (8)
<223> OTHER INFORMATION: 2/4-thiouracil
<220> FEATURE:
<221> NAME/KEY: modified_base
<222> LOCATION: (9)
<223> OTHER INFORMATION: Diaminopurine
<220> FEATURE:
<221> NAME/KEY: modified_base
<222> LOCATION: (10)
<223> OTHER INFORMATION: Thioguanine
<220> FEATURE:
<221> NAME/KEY: modified_base
<222> LOCATION: (11)
<223> OTHER INFORMATION: Diaminopurine

<400> SEQUENCE: 5
cnnnnntnnn nc                                                               12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)
<223> OTHER INFORMATION: Pyrimidone
<220> FEATURE:
<221> NAME/KEY: modified_base
<222> LOCATION: (9)..(10)
<223> OTHER INFORMATION: Pyrimidone

<400> SEQUENCE: 6
gtntaattnn ag                                                               12
```

```
<210> SEQ ID NO 7
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic PNA sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: Diaminopurine
<220> FEATURE:
<221> NAME/KEY: modified_base
<222> LOCATION: (2)
<223> OTHER INFORMATION: Thioguanine
<220> FEATURE:
<221> NAME/KEY: modified_base
<222> LOCATION: (5)
<223> OTHER INFORMATION: Thioguanine
<220> FEATURE:
<221> NAME/KEY: modified_base
<222> LOCATION: (6)..(7)
<223> OTHER INFORMATION: Diaminopurine
<220> FEATURE:
<221> NAME/KEY: modified_base
<222> LOCATION: (8)
<223> OTHER INFORMATION: Thioguanine
<220> FEATURE:
<221> NAME/KEY: modified_base
<222> LOCATION: (10)
<223> OTHER INFORMATION: 2/4-thiouracil
<220> FEATURE:
<221> NAME/KEY: modified_base
<222> LOCATION: (12)
<223> OTHER INFORMATION: 2/4-thiouracil

<400> SEQUENCE: 7
nntcnnnngn cn                                                              12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (5)
<223> OTHER INFORMATION: Pyrimidone
<220> FEATURE:
<221> NAME/KEY: modified_base
<222> LOCATION: (8)
<223> OTHER INFORMATION: Pyrimidone
<220> FEATURE:
<221> NAME/KEY: modified_base
<222> LOCATION: (11)
<223> OTHER INFORMATION: Pyrimidone

<400> SEQUENCE: 8
agacnttnga nt                                                              12

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (3)..(4)
```

```
<223> OTHER INFORMATION: Diaminopurine
<220> FEATURE:
<221> NAME/KEY: modified_base
<222> LOCATION: (5)..(6)
<223> OTHER INFORMATION: Inosine

<400> SEQUENCE: 9 tcnnnntaca                                                              10

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA sequence
<220> FEATURE:
<221> NAME/KEY: modified_base
<222> LOCATION: (1)
<223> OTHER INFORMATION: Diaminopurine
<220> FEATURE:
<221> NAME/KEY: modified_base
<222> LOCATION: (4)
<223> OTHER INFORMATION: Diaminopurine
<220> FEATURE:
<221> NAME/KEY: modified_base
<222> LOCATION: (9)
<223> OTHER INFORMATION: Diaminopurine

<400> SEQUENCE: 10
ngtntcgtnc cg                                                           12

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA sequence

<400> SEQUENCE: 11
tcaaggtaca                                                              10
```

MONOMERIC AND POLYMERIC LINKERS USEFUL FOR CONJUGATING BIOLOGICAL MOLECULES AND OTHER SUBSTANCES

This application is a national stage filing under 35 U.S.C. §371 of International Application No. PCT/IB2006/002584 filed on Jun. 30, 2006. This international application also claims priority to three U.S. Provisional Patent Application Nos.: 60/695,408; 60/695,409; and 60/695,410; each of which was filed on Jul. 1, 2005. All of those applications are incorporated by reference herein.

The present invention concerns monomeric or polymeric linkers useful in biological and chemical applications, their synthesis, and the synthesis and use of derivatives of the linkers conjugated to a variety of detectable labels and other substances. The linkers may be used, for example, in conjunction with fluorescent labels, nucleic acid or nucleic acid analog probes, and solid phase systems, and to enhance the solubility of conjugated atoms, groups, or molecules.

BACKGROUND AND SUMMARY OF THE INVENTION

Large molecules and detectable labels such as fluorophores, solid phase matrices or beads, antibodies, and hybridization probes are frequently attached to other molecules indirectly via linkers in order to avoid steric clashes which could decrease the affinity between those molecules and their targets, thus reducing their biological activity. A "linker" is a molecule that serves to join other atoms, molecules, or functional groups together via covalent or non-covalent interactions.

Ideally, a linker may separate an attached detectable label from a target molecule, without detracting from the useful properties of the detectable label, such as its signal intensity, binding affinity, or solubility. In practice, however, many linker molecules used in the art have a relatively short length, making it difficult to avoid steric clashes between the substances that they serve to juxtapose. For example, linkers such as 6-amino-hexanoic acid, succimidyl 4-(N-malemidomethyl)cylohexane-1-carboxylate (SMCC), and N-γ-malemidobutyryloxy succinimide ester (GMBS); are between 7 and 9 atoms in length, which would correspond to about 1 nm if they are fully extended in solution. That length is only a small fraction of the size of the average biological macromolecule such as a protein or oligonucleotide, and may be insufficient to relieve potential steric dashes between atoms, groups, or molecules to which those linkers are conjugated. Other examples of relatively short linkers used in the art include homobifunctional linkers such as glutaricdialdehyde, divinylsultone, hexane di-isocyanate, dimethylapimidate, 1,5-difluoro-2,4-dinitrobenzene, heterobifunctional linkers such as N-gamma-maleimidobytyroloxy succinimide ester, and zero length linkers such as 1-ethyl-3-(3-dimethylaminopropyl)cabodiimide.

Longer linker molecules based upon polyethylene glycol (PEG) are also available in the art. (See, for example, Discrete PEG (dPEG)™ modification reagents available from Quanta Biodesign, Ltd., Powell, Ohio, or at www.quantabiodesign.com; PEG-based reagents available from EMD Biosciences, Inc., San Diego, Calif., described in Novabiochem April, 2004, "Product focus: PEG reagents—bifunctional amino-PEG-acid spacers" brochure, available at www.novabiochem.com; and see Baumeister et al., *Biopolymers*, 71: 339 (2003); Kumar & Aldrich, *Org. Lett.*, 5: 613 (2003). (See also, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA.) While PEG-based linkers have a longer length, for example from 20 to over 70 atoms, they may not always remain extended in solution, and instead may aggregate or form unwanted tertiary structures. Such unwanted homo- or hetero-aggregation can negatively affect the activity of the conjugated atoms, groups, or molecules.

One object of the present invention was to find a linker structure that could adopt a variety of lengths, including very long lengths, that may have a well defined molecular and structural formula even at very long lengths, that would have less tendency to form unwanted tertiary structures or aggregates, that could readily and efficiently polymerize if desired, and that would exist in extended form in solution. The linkers of the present invention may allow for different conjugated atoms, groups, or molecules to be separated by short distances or by, for instance, up to several nanometers in solution. The instant linkers also may be designed such that they possess well defined molecular and structural formulas, providing greater uniformity to molecular entities that comprise them. In some of the instant embodiments, even very long linkers according to the present invention surprisingly remain in an extended and flexible structure in aqueous solutions and have little tendency to fold inward upon themselves, aggregate with each other, or form other tertiary structures that interfere with the functions of the conjugated atoms, groups, or molecules that they carry. Some of the instant linkers form chains with little steric bulk along their length, and thus may easily access narrow molecular spaces to interact with solid phase surfaces or membranes at a high density. The present invention also comprises methods of synthesizing the instant linkers and attaching them covalently to other molecules and functional groups at high yield.

The linkers of the present invention may be covalently or non-covalently attached to a variety of substances including color labels, components of solid surfaces, nucleic acids and nucleic acid analogs, proteins, and protein substrates. The ability of some of the instant linkers to remain extended and flexible in solution can minimize steric interference between the linker and the conjugated atom, group, or molecule, so that the conjugate's signal or its availability for recognition by target molecules is minimally perturbed by the linker. Thus, the present invention comprises a method of enhancing the signal intensity, activity, or binding affinity of a molecule such as a detectable label, including a probe, comprising conjugating the molecule to one or more of the instant linkers.

For example, when protein-nucleic acid (PNA) probes are conjugated to the linkers, the PNAs are less susceptible to aggregation and remain more available for binding to their intended target sequences. Further, because the structure of the instant linkers in solution may be both long and flexible, the instant linkers may be used to cross-link large molecules together in a way that allows the molecules to adopt their preferred orientations, and thus, minimally perturbs the structure and affinity of the Molecular complex.

As another example, steric bulk or tertiary structure near a fluorescent label can cause quenching of the fluorescence due to absorbance of the signal by the surrounding molecular bonds. Interactions between two or more nearby fluorophores may also cause their signals to quench. This may be a problem in designing detectable labels comprising multiple conjugated fluorophores. For example, in protein detection, typically only about 3-4 fluorophores may be added before a plateau is reached in the intensity of the signals. The addition of further fluorophores may even diminish the overall signal. Such quenching may be reduced using embodiments of the present invention. Accordingly, this invention includes a method of enhancing the signal of one or more fluorophores, comprising conjugating the one or more fluorophores to at least one of the instant linkers. Because quenching due to the linker attachment of the present invention may be minimal, and because individual fluorophores may be conjugated so that they do not significantly interfere with each other, the present linkers also allow for the design of multiple-fluorophore linker derivatives having predictable emission colors that are a combination of the emissions from individual fluorophores of different emission spectra.

Another surprising feature of some of the present linkers is their high water solubility despite a relatively limited number of polar or charged groups. The instant linkers may enhance the solubility of a variety of different conjugated atoms, groups, or molecules. Thus, this invention also comprises a method of enhancing the solubility of a conjugated atom, group, or molecule, comprising directly or indirectly conjugating one or more atoms, groups, or molecules to one or more of the instant linkers.

Additional objects and advantages of the invention will be set forth in the description which follows, will be obvious from the description, or may be learned by practice of the invention. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitutes a part of this specification, illustrate some of the embodiments of the invention and, together with the description, serves to explain some of the principles of the invention.

FIG. 5 depicts exemplary capture assays using the instant linkers conjugated to probes.

FIG. 6 depicts exemplary non-natural nucleobases.

DETAILED DESCRIPTION OF THE INVENTION

A. Linkers

Figure 1:
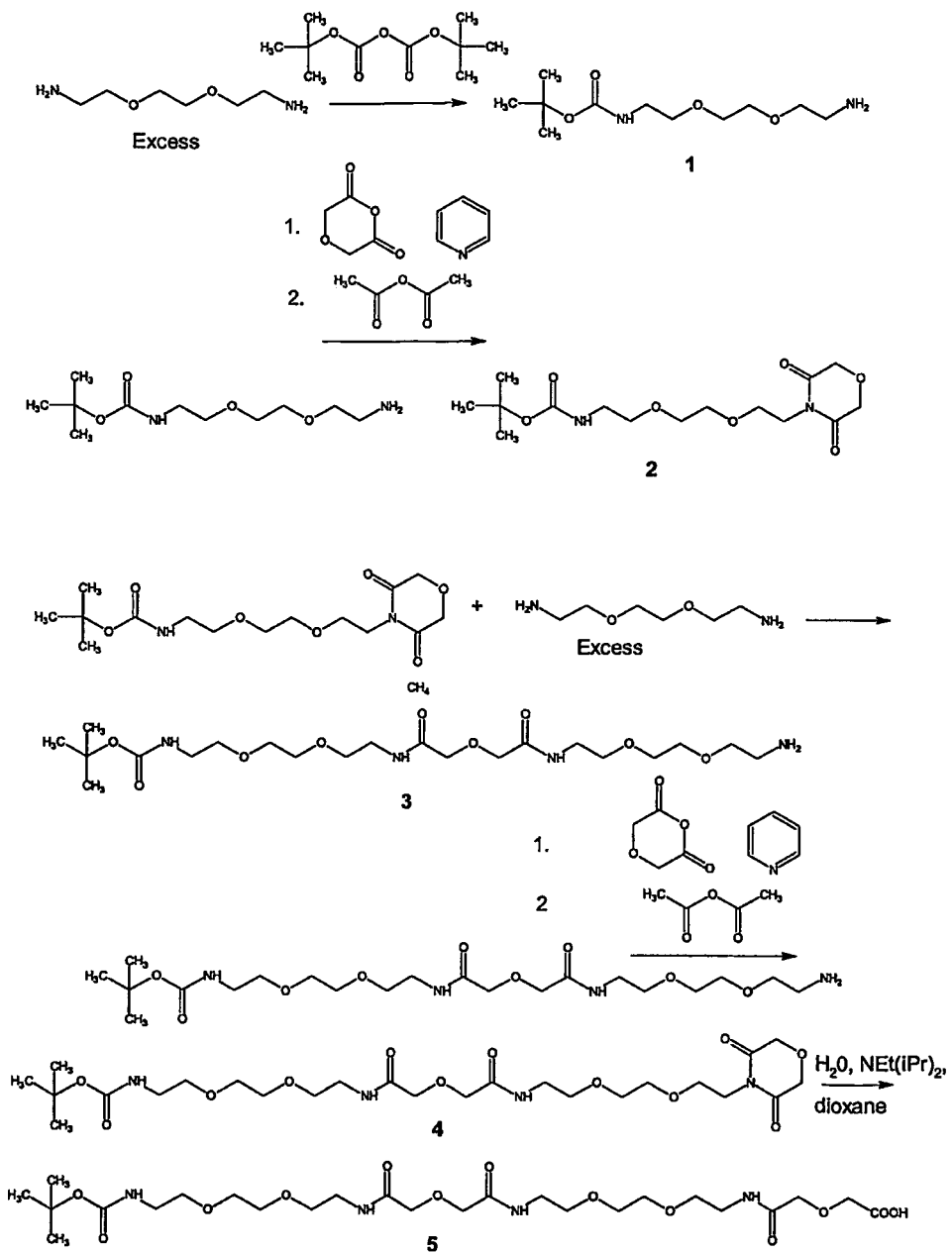
FIG. 1 depicts a synthesis of an exemplary L15 linker unit derived from 3,9,12-trioxa-6,15-diaza-5-oxo-pentadecanoic acid, and the synthesis of an exemplary L30 linker according to the present invention.

The instant "linker" is a molecule that may help to join other atoms, molecules, or functional groups together through chemical bonds. For example, one of the instant linkers may be conjugated to a protein as well as to another group such as a fluorophore, joining those substances together through the intervening chemical bonds in the linker.

In some embodiments of the invention, the "linker" comprises a molecular entity derived from the reaction of at least one amine, such as a diamine, and a di-carboxylic acid anhydride. In some embodiments, the amine comprises no more than two ethyleneoxy ($CH_2$—$CH_2$—O) units. For example, the instant "linker" may comprise an alternating copolymer of such amine and di-carboxylic acid anhyride-derived units. In some embodiments, the amine comprises a structural formula with no more than two methylene units in a row. For example, the amine may comprise a structural formula such as: $NH_2$—$CH_2$—$CH_2$—O—$CH_2$—$CH_2$—O—$CH_2$—$CH_2$—$NH_2$ or $NH_2$—$CH_2$—$CH_2$—O—$CH_2$—$CH_2$—O—$CH_2$—$CH_2$—O—$CH_2$—$CH_2$—$NH_2$, or other structural formulas in which a heteroatom is placed after every two methylene units.

In some embodiments of this invention, the "linker" comprises at least one monomeric unit referred to herein as "L15." In other embodiments, the instant "linker" comprises two or more L15 units arranged in a linear or branched fashion. For example, in some embodiments, the linker is a linear polymer chain comprising two L15 units, called "L30" herein. In yet other embodiments, the linker comprises a longer linear polymer comprising several L15 units, and may be called, for example, "L45," or "L60," "L90," or "L120," or "L300," and so forth herein, depending on the number of L15 units the polymer chain comprises. In some embodiments comprising more than one L15 unit, the L15 units may be connected covalently via one or more intervening chemical bonds:

In some embodiments of this invention, L15 comprises the unit shown below in Formula I.

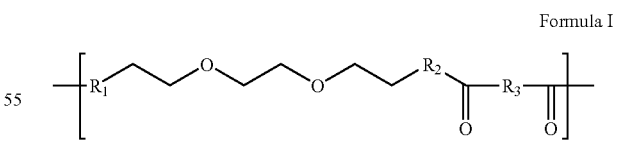

Formula I

In Formula I, $R_1$ and $R_2$ may comprise either NH or O, while $R_3$ may comprise methyl, ethyl, propyl, $CH_2$—O—$CH_2$, and ($CH_2$—O—$CH_2$)$_2$. Further, when Formula I is conjugated to other groups, atoms, or molecules, and, for instance, $R_1$ and/or $R_2$ is an oxygen, no more than three consecutively repeating ethyleneoxy ($CH_2$—$CH_2$—O) groups are present.

Thus, some of the L15 units according to this invention may have the following molecular structures:

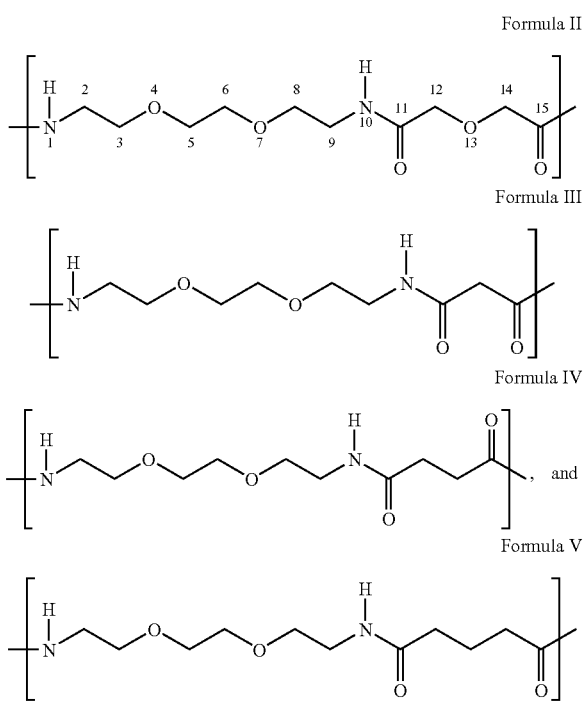

Formula II

Formula III

Formula IV

Formula V

Other possible L15 structures not shown above may be envisioned based upon the choice of $R_1$, $R_2$, and $R_3$ groups.

In some embodiments, the instant linkers are comprised of a linear polymer of L15 units in which each L15 unit has the same molecular formula, for example, that of structural formula II. In other embodiments, one or more L15 units may differ from the others in the linker chain. For example, a linker may comprise several units of formula II, and one or more units comprising one or more different structures. Such a differing L15 unit may be useful in attaching a particular atom, group, or molecule at a defined location in the chain, for example. Because each unit may be added iteratively to the growing linker chain, such as by solid phase synthesis, a variety of mixed L15 polymers may be constructed simply and in a controlled fashion.

In some embodiments, one or more of the heteroatom groups in the linker comprises a further substituent. That substituent may comprise a variety of atoms or functional groups such as a simple hydrogen atom, a protecting group, or a conjugating group which serves to attach the linker to a atom, group, or molecule. In some embodiments, the substituent is a detectable label or another linker. Attachment via the heteroatom groups to a further linker forms a branched linker polymer.

B. Design and Synthesis of Linkers

The present invention also comprises novel methods of synthesizing an L15 linker and linear polymers of the L15 linker in high yield. According to this synthesis method, long linkers of, for example, L120, L200, L300, or even longer, such as L600 or L990, may be constructed by consecutive additions of L15 units or portions of L15 units, for example, on solid phase. Alternatively, long linkers may be formed by joining two intermediate length linkers together. Linkers of L30 or larger synthesized according to this method may comprise individual L15 units of the same or different molecular structure.

L15 units according to this invention may be prepared by contacting a protected amine with a di-carboxylic acid anhydride and acetic anhydride, resulting in a cyclic imide terminal group, which may then be opened once the linker reaches its desired length, for instance by basic aqueous hydrolysis in dioxane using a tertiary amine such as diisopropylethyl amine. A 3,9,12-trioxa-6,15-diaza-5-oxo-pentadecanoic acid molecule has been synthesized from 2,2'-(ethylenedioxy)bis (ethylamine) at about 87-91% yield (see Pieters et al., *Bioorg. Med. Chem. Lett.* 9: 161-6 (1999)). In contrast, the controlled methods of synthesizing L15 units according to the present invention may provide yields of 96%, for example.

The synthesis may be carried out in solution. The amine may be protected with (Boc)$_2$O, monomethoxytrityl (MMT), benzyloxycarbonyl (Z), or fluorenylmethyloxycarbonyl (Fmoc), or another suitable protecting group. In some embodiments, the amine is 2,2'-(ethylenedioxy)bis(ethylamine) (structure 1 of FIG. 1). In some embodiments, the amine is present in excess over the di-carboxylic acid anhydride and acetic anhydride. The addition of the di-carboxylic acid anhydride may be carried out at a wide range of temperature. Suitable di-carboxylic acid anhydrides include those from diglycolic acid, 1,5-dipentanoic acid, 1,4-dibutyric acid, 1,3 dipropanoic acid, and 3,6 dioxaoctane dioic acid, depending on the desired $R_3$ group. Subsequent addition of acetic anhydride may force the product into the cyclic imide form in high yield. (Structure 2 of FIG. 1.) The cyclic imide may be quantitatively opened if desired, for example, in excess dioxane and di-isopropylethylamine (DIPEA). To initiate the preparation of an L30 linker, the cyclic imide may be reacted with another amine. (Structure 3 of FIG. 1.) Then, di-carboxylic acid anhydride and acetic anhydride may be added and the resulting cyclic imide opened. (Structure 4 of FIG. 1.) In some embodiments, the terminal cyclic imide on the linker may be left unopened in order to serve as a reactive group for the formation of other bonds such as to reactive groups or other attachments.

For example, a 3,9,12-trioxa-6,15-diaza-5-oxo-pentadecanoic acid-derived L15 monomer may be prepared by protecting one of the two amine groups of 2,2'-(ethylenedioxy) bis(ethylamine) with (Boc)$_2$O. (See FIG. 1, reaction scheme 1, part A.) After dissolving the mono-protected 2,2'-(ethylenedioxy)bis(ethylamine) (structure 1 of FIG. 1) in pyridine, diglycolic acid and then acetic anhydride may be added at high temperature, such as at about 100° C., to form a cyclic L15 structure (structure 2 of FIG. 1). Excess 2,2'-(ethylenedioxy)bis(ethylamine) reacts with the cyclic imide to form structure 3, shown in FIG. 1. To form an L30 linker, an additional diglycolic acid may be added, and the cyclic terminal opened by addition of 1,4 dioxane and diisopropylethylamine (DIPEA) in aqueous solution.

In some embodiments of the invention in which one or both of $R_1$ and $R_2$ are oxygens rather than amine groups, aminoalcohols or di-alcohols may be substituted for the amine in the reactions described above. Conditions may also be adjusted to account for the different reactivities of alcohols and amines. For instance, reactions may be run at higher temperatures when coupling with alcohols rather than amines.

Using the instant methods, large batches, such as 100 g, of protected L30 linkers may be prepared in pure form by an extractive work-up using one liter-scale laboratory equipment. The examples below provide a more detailed description of the synthesis of exemplary molecules comprising L15 and L30 linkers according to this invention.

The same synthetic principles apply to the preparation of larger linker polymer chains used in some embodiments of this invention. For example, linkers such as L45, L60, L90, L120, L150, L200, L300, or even larger, for instance, comprising as many as 40 L15 units, may be prepared by repeating the steps described above successively: first reacting the cyclic imide of the preceding L15 unit in the growing chain with excess amine, and adding acid anhydride and then acetic anhydride to build on a further L15 unit. Once the desired length is achieved, the terminal ring may be opened. If desired, those successive steps may also be performed on solid support, which may be convenient in preparing linkers longer than L30 or L60, for example In fact, compounds of molecular weights of 8 to 15 KDa may be prepared with the methods of the present invention because successive synthetic steps are not inhibited by the growing poly-L15 chains. This is quite unusual for peptide chemistry.

Alternatively, to shorten the number of steps needed to prepare longer linkers, intermediate length linkers such as L30, for example, can be directly combined together or conjugated indirectly through an intervening chemical group such as a reactive group or a detectable label. For instance, a single chromatographic purification step allows the preparation of high purity Boc-L30, which may be readily oligomerized to prepare longer linkers such as L300 at high purity. Even linkers such as L600 and longer such as L1000 may be prepared by such methods, the only limitations being the yield of each step and the amount of materials available. Further, two long linkers may be joined along their chains to form very long branched linkers comprising, for instance, as many as 10, 20, 40, or even 60 L15 units in total.

Because it is possible to control the synthesis conditions, the present invention further comprises linkers and linker derivatives comprising a homogeneous molecular and structural formula. A homogeneous molecular formula means herein that the molecular weight of the linker may be obtained via mass spectrometry with less than 1% deviation from the expected molecular weight based upon the synthesis protocol used, in some embodiments less than 0.1% or even less than 0.01%. This is possible even with very long linkers such as L300, L600; or L990. A homogeneous structural formula means herein that the structural composition of each L15 unit and its location within the linker chain is controlled by the synthesis protocol used to prepare the linker. In contrast, many PEG-based linkers comprise a mixture of lengths and structural formulae. Thus, substances that comprise those mixed linkers inherently are heterogeneous, regardless of the purity or homogeneity of the molecules, groups, or atoms to which the linkers were conjugated.

Many currently used linkers, such as certain nucleic acid or nucleic acid analog-based linkers, carry a charge on each monomer of the chain, for example, from a backbone phosphate or phosphorothioate group. Such charges may cause those linkers to aggregate with substances of opposite charge, including the walls of a plate or vessel, or to attract unwanted metal ions, or to precipitate in the presence of salts. In contrast, the instant linkers may be designed such that they carry no charge, or only one or a few charges at defined locations along the chain. Because one may control the synthesis of the instant linkers, they may be designed to place charges at only specific locations or to carry no charges at all. This allows for a precise modulation of the location and amount of charge in a given linker and linker derivative and is a further method of avoiding unwanted aggregation or tertiary interactions.

Nevertheless, for some embodiments, the instant linkers may also be prepared using an uncontrolled polymerization reaction. For example, a one-pot synthesis may be conducted based upon the reaction steps above, such as by mixing a diamine in solution with an excess of di-carboxylic anhydride. The synthesis may also be terminated, for example, by adding a reagent that would form an end group, such as an amino acid or fluorophore. Controlling the amount of such a terminating reagent may help dictate the actual length distribution of the mixture. Such methods may be useful, for instance, when absolute length is unimportant, or to generate linkers of a variety of different lengths at once. The products may be fractionated by length, for instance by chromatography.

C. Linker Derivatives

Linkers of the present invention may be covalently bound to another atom, group, or molecule to form a "linker derivative." Linker derivatives may comprise only one linker conjugated to another atom, group, or molecule, or may comprise multiple linkers conjugated to more than one of the same atom, group, or molecule, or conjugated to different atoms, groups, or molecules. The binding of the atom, group, or molecule may occur at one or more free ends of the linker, or along its length such as at one of its heteroatoms. Examples of atoms, groups, or molecules that may be conjugated to linkers to form linker derivatives include hydrogen atoms, terminal groups such as protecting groups, methyl groups, or acetyl groups. Other examples include heavy or radioactive isotopes, leaving groups; fluorophores; chromophores; enzyme substrates; antigens; antibodies; other proteins and peptides; amino acids and amino acid analogs; nucleic acids and nucleic acid analogs; components of a membrane or a solid support; and other small or large molecules. Linkers according to this invention may thus be conjugated to several atoms, groups, or molecules of the same type, such as multiple fluorophores, or may be conjugated to different types of groups or molecules, such as a PNA and a fluorophore or a protein and a solid surface or an acetyl group and an antibody. The covalent binding may be direct, with no intervening bonds or atoms, or indirect, with one or more intervening bonds or atoms. As used herein, any atom, group, or molecule that is covalently attached to a linker, either directly or indirectly, is "conjugated to" the linker. Hence, "linker derivatives" include molecular entities referred to as "conjugates." Atoms, groups, or molecules may also be non-covalently attached to the instant linkers or linker derivatives, for example, by adsorption on a surface, intercalation, hybridization of complementary nucleic acids or nucleic acid analogs, or other interactions.

Atoms, groups, or molecules may be conjugated at one end of the linker, or the same or different atoms, groups, or molecules may be placed at both ends. Alternatively, conjugated atoms, groups, or molecules may be placed between two linkers, for example, at a defined spacing that prevents unwanted interactions between them. Hence, linker derivatives such as X-L, L-X, or X-L-X or L-X-L may be prepared where X represents a directly or indirectly conjugated atom, group, or molecule and L represents a linker. Such linker derivatives can also include different atoms, groups, or molecules, for example, X1-L-X2, or X1-L1-X2-L2 or L1-X1-L2-X2. An atom, group, or molecule can also be conjugated, for example, via one of the heteroatoms in the linker. In addition, several linkers may be conjugated to one linker derivative to form branched structures. Linkers conjugated to multiple atoms, groups, or molecules such as color labels or radioactive isotopes are advantageous, for example, in amplifying signals in detection assays as an alternative to antibody-based amplification methods and radioactivity.

1. Indirect Conjugation

A linker may be conjugated to another group, atom, or molecule indirectly through a group that is more reactive with the anticipated atom, group, or molecule than the linker itself. As used herein, such groups are called "conjugating groups." In some embodiments, the linkers are conjugated to carbodiimide-based conjugating groups. Amino acids may also serve as conjugating groups. For example, amino acids with amino side chains may be used to conjugate, for example, fluorophores. The sulfhydryl of cysteine is also useful as a conjugating group for forming disulfide crosslinks to other substances. In some embodiments, the linkers are conjugated to Lys(Cys), which is a C-terminal lysine-carboxamide with a cysteine amino acid bound to the N of the lysine side-chain, and which may serve as a conjugating group. The juxtaposed amine and sulfhydryl groups of this cysteine moiety unexpectedly provided significantly higher reactivity toward dextran, for example, than carbodiimide conjugating groups.

In some embodiments, the linker is conjugated to amino groups such as to a lysine amino acid in which the N is derivatized with beta-alanine-N,N-diacetic acid. The lysine derivative can be quantitatively converted into its cyclic N-2,6-Dioxo-morpholino anhydride form. That form was highly amino reactive under weakly basic aqueous conditions when compared to previously used amino reactive groups such as NHS-esters. Hence, it may also serve as a conjugating group. One of ordinary skill in the art may readily envision other conjugating groups that may be conjugated to the instant linkers in order to assist in conjugating a variety of substances to the instant linkers.

2. Detectable Labels

In some embodiments, one or more detectable labels are conjugated to a linker. According to this invention, a "detectable label" is any molecule or functional group that allows for the detection of a biological or chemical characteristic or change in a system, such as the presence of a target substance in the sample.

Examples of detectable labels which may be used in the invention include fluorophores, chromophores, electrochemiluminescent labels, bioluminescent labels, polymers, polymer particles, bead or other solid surfaces, gold or other metal particles or heavy atoms, spin labels, radioisotopes, enzyme substrates, haptens, antigens, Quantum Dots, aminohexyl, pyrene, nucleic acids or nucleic acid analogs, or proteins, such as receptors, peptide ligands or substrates, enzymes, and antibodies (including antibody fragments).

Examples of polymer particles labels which may be used in the invention include micro particles, beads, or latex particles of polystyrene, PMMA or silica, which can be embedded with fluorescent dyes, or polymer micelles or capsules which contain dyes, enzymes or substrates. Examples of metal particles which may be used in the invention include gold particles and coated gold particles, which can be converted by silver stains. Examples of haptens that may be conjugated in some embodiments are fluorophores, myc, nitrotyrosine, biotin, avidin, strepavidin, 2,4-dinitrophenyl, digoxigenin, bromodeoxyuridine, sulfonate, acetylaminoflurene, mercury trintrophonol, and estradiol.

Examples of enzymes which may be used in the invention comprise horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, and glucose oxidase (GO). Examples of commonly used substrates for horse radish peroxidase (HRP) include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), alpha-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF). Examples of commonly used substrates for Alkaline Phosphatase include Naphthol-AS-B1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphate/fast red TR (NAMP/FR), Naphthol-AS-B1-phosphate/new fuschin (NABP/NF), bromochioroindolyl phosphate/nitroblue tetrazolium (BCIP/NBT), 5-Bromo-4-chloro-3-indolyl-beta-delta-galactopyranoside (BCIG).

Examples of luminescent labels which may be used in the invention include luminol, isoluminol, acridinium esters, 1,2-dioxetanes and pyridopyridazines. Examples of electrochemiluminescent labels include ruthenium derivatives. Examples of radioactive labels which may be used in the invention include radioactive isotopes of iodide, cobalt, selenium, hydrogen, carbon, sulfur, and phosphorous.

Some "detectable labels" according to this invention comprise "color labels," in which the biological change or event in the system may be assayed by the presence of a color, or a change in color. Examples of "color labels" are chromophores, fluorophores, chemiluminescent compounds, electrochemiluminescent labels, bioluminescent labels, and enzymes that catalyze a color change in a substrate.

"Fluorophores" as described herein are molecules that emit detectable electro-magnetic radiation upon excitation with electro-magnetic radiation at one or more wavelengths. A large variety of fluorophores are known in the art and are developed by chemists for use as detectable molecular labels and can be conjugated to the linkers of the present invention. Examples include fluorescein or its derivatives, such as fluorescein-5-isothiocyanate (FITC), 5-(and 6)-carboxyfluorescein, 5- or 6-carboxyfluorescein, 6-(fluorescein)-5-(and 6)-carboxamido hexanoic acid, fluorescein isothiocyanate, rhodamine or its derivatives such as tetramethylrhodamine and tetramethylrhodamine-5-(and-6)-isothiocyanate (TRITC). Other example fluorophores that could be conjugated to the instant linkers include: coumarin dyes such as (diethyl-amino)coumarin or 7-amino-4-methylcoumarin-3-acetic acid, succinimidyl ester (AMCA); sulforhodamine 101 sulfonyl chloride (TexasRed™ or TexasRed™ sulfonyl chloride; 5-(and-6)-carboxyrhodamine 101, succinimidyl ester, also known as 5-(and-6)-carboxy-X-rhodamine, succinimidyl ester (CXR); lissamine or lissamine derivatives such as lissamine rhodamine B sulfonyl Chloride (LisR); 5-(and-6)-carboxyfluorescein, succinimidyl ester (CFI); fluorescein-5-isothiocyanate (FITC); 7-diethylaminocoumarin-3-carboxylic acid, succinimidyl ester (DECCA); 5-(and-6)-carboxytetramethylrhodamine, succinimidyl ester (CTMR); 7-hydroxycoumarin-3-carboxylic acid, succinimidyl ester (HCCA); 6→fluorescein-5-(and-6)-carboxamidolhexanoic acid (FCHA); N-(4,4-difluoro-5,7-dimethyl-4-bora-3a,4a-diaza-3-indacenepropionic acid, succinimidyl ester; also known as 5,7-dimethylBODIPY™ propionic acid, succinimidyl ester (DMBP); "activated fluorescein derivative" (FAP), available from Probes, Inc.; eosin-5-isothiocyanate (EITC); erythrosin-5-isothiocyanate (ErITC); and Cascade™ Blue acetylazide (CBAA) (the O-acetylazide derivative of 1-hydroxy-3,6,8-pyrenetrisulfonic acid). Yet other potential fluorophores useful in this invention include fluorescent proteins such as green fluorescent protein and its analogs or derivatives, fluorescent amino acids such as tyrosine and tryptophan and their analogs, fluorescent nucleosides, and other fluorescent molecules such as Cy2, Cy3, Cy 3.5, Cy5, Cy5.5, Cy 7, IR dyes, Dyomics dyes, phycoerythrine, Oregon green 488, pacific blue, rhodamine green, and Alexa dyes. Yet other examples of fluorescent labels which may be used in the invention include and conjugates of R-phycoerythrin or allophycoerythrin, inorganic fluorescent labels such as particles based on semiconductor material like coated CdSe nanocrystallites.

A number of the fluorophores above, as well as others, are available commercially, from companies such as Probes, Inc. (Eugene, Oreg.), Pierce Chemical Co. (Rockford, Ill.), or Sigma-Aldrich Co. (St. Louis, Mo.).

In some embodiments the detection unit may comprise from 1 up to 500 detectable label molecules. In some embodiments, the detectable label is an enzyme, which may be conjugated to a polymer, such that the number of enzyme molecules conjugated to each polymer molecule is, for instance, 1 to 200, 2 to 50, or 2 to 25. In some embodiments, the detectable label is a gold particle, a radioactive isotope, or a color label, e.g. a low molecular weight fluorophore, and the number of detectable labels conjugated to each polymer molecule is, for instance, 1 to 500, or for instance, 2 to 200. In some embodiments, the detectable label is a protein fluorophore and the number of detectable labels conjugated to each polymer molecule is 1-50, 2-20. In some embodiments, the number of detectable label molecules conjugated to each polymer is 1-200, 2-50, 2-25, or is 10-20, 5-10, or 1-5.

The detectable label can be detected by numerous methods, including, for example, reflectance, transmittance, light scatter, optical rotation, and fluorescence or combinations hereof in the case of optical labels or by film, scintillation counting, or phosphorimaging in the case of radioactive labels. See, e.g., Larsson, 1988, *Immunocytochemistry: Theory and Practice*, (CRC Press, Boca Raton, Fla.); *Methods in Molecular Biology*, vol. 80 1998, John D. Pound (ed.) (Humana Press, Totowa, N.J.). In some embodiments, more than one detectable label is employed.

3. Probes

Some linker derivatives according to this invention may be comprise a conjugated "probe" which, as used herein, is a functional group or molecule which monitors events or changes in a system, for example, by binding, reacting with, or hybridizing to a target substance in the system directly or indirectly. An example of a probe is a nucleic acid or nucleic acid analog capable of binding to or hybridizing with a particular target sequence. Other examples include antibodies, such as primary or secondary antibodies, antigens, enzyme substrates and protein ligands, haptens, proteins, and peptides.

4. Antibodies

In some embodiments, the instant linker derivatives comprise, for example, at least one polyclonal, monoclonal, monospecific, polyspecific, humanized, single-chain, chimeric, synthetic, recombinant, hybrid, mutated, and CDR-grafted antibodies. Various techniques for producing antibodies and preparing recombinant antibody molecules are known in the art and have been described, see, e.g., Kohler and Milstein, (1975) *Nature* 256:495; Harlow and Lane, *Antibodies: a Laboratory Manual*, (1988) (Cold Spring Harbor Press, Cold Spring Harbor, N.Y.). Antibodies used in the invention may be derived from any mammal species, e.g., rat, mouse, goat, guinea pig, donkey, rabbit, horse, lama, camel, or any avian species e.g., chicken, duck. The origin of the antibody is defined by the genomic sequence irrespective of the method of production.

The antibody may be of any isotype, e.g., IgG, IgM, IgA, IgD, IgE or any subclass, e.g., IgG1, IgG2, IgG3, IgG4. The skilled artisan will appreciate that antibodies produced recombinantly, or by other means, for use in the invention include any antibody fragment which can still bind antigen, e.g. an Fab, an $F(ab)_2$, Fv, scFv. In certain embodiments, the antibody, including an antibody fragment, may be recombinantly engineered to include a hapten, e.g., a peptide. In certain embodiments the hapten may be a myc tag (se FIG. 6N). Inclusion of a hapten in an antibody or antibody fragment facilitates subsequent binding of a binding agent, probe, or label Certain embodiments employ linker derivatives comprising a primary antibody containing an antigen binding region. Some embodiments employ linker derivatives comprising a secondary antibody containing an antigen binding region which specifically binds to a primary antibody, e.g., the constant region of the primary antibody. In certain embodiments, the linker derivative is further conjugated to a polymer. Some embodiments employ linker derivatives comprising a tertiary antibody containing an antigen binding region which specifically binds to the secondary antibody, e.g., a constant region of the secondary antibody, or a hapten linked to the secondary antibody or a polymer conjugated to the secondary antibody. In certain embodiments; the tertiary antibody is further conjugated to a polymer.

5. Nucleic Acids and Nucleic Acid Analogs

In some embodiments, the linker is conjugated to at least one nucleic acid and/or nucleic acid analog. As used herein, a "nucleic acid" refers to a nucleobase sequence comprising any oligomer, polymer, or polymer segment, having a backbone formed solely from RNA or DNA nucleosides and comprising only the bases adenine (A), cytosine (C), guanine (G), thymine (T), and uracil (U), wherein an oligomer means a sequence of two or more nucleobases. Nucleic acids may also be referred to as nucleic acids.

Figure 9:
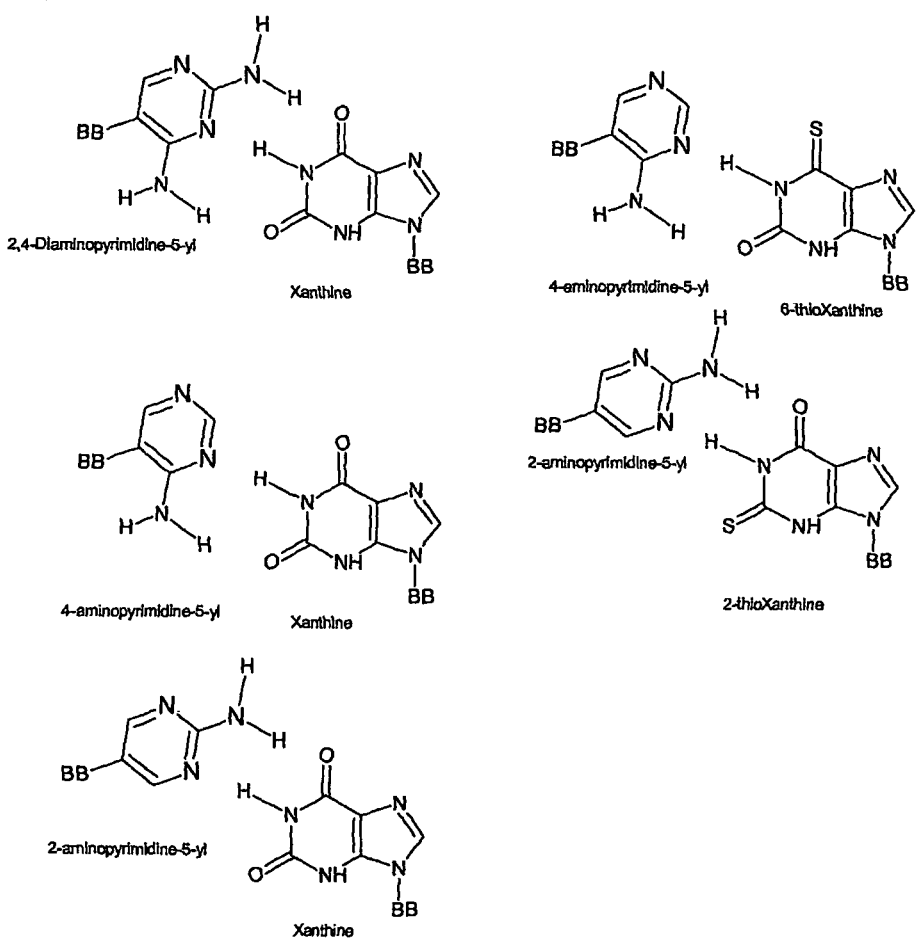
FIG. 9 depicts additional exemplary non-natural nucleobases and base pairs.

Non-natural bases may include, for example, purine-like and pyrimidine-like molecules, such as those that may interact using Watson-Crick-type, wobble, or Hoogsteen-type pairing interactions. Examples include generally any nucleobase referred to elsewhere as "non-natural" or as an "analog." FIGS. 6 and 9 depict a few examples.

Examples include: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine).

Yet other examples include bases in which one amino group with a hydrogen is substituted with a halogen (small "h" below), such as 2-amino-6-"h"-purines, 6-amino-2-"h"-purines, 6-oxo-2-"h"-purines, 2-oxo-4-"h"-pyrimidines, 2-oxo-6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines.

For example, some specific embodiments of non-natural bases are the structures shown in FIG. 6 with the following substituents: These and other non-natural bases are described further below and in the accompanying International Application entitled "New Non-Natural Base Pairs."

| Base (Symbol) | R2 | R3 | R4 | R5 | R6 |
|---|---|---|---|---|---|
| A | H or $CH_3$ | H | H | | |
| isoA | H or $CH_3$ | H | H | | |
| D | H or $CH_3$ | H | | | |
| G | H or $CH_3$ | H | | | |

| Base (Symbol) | R2 | R3 | R4 | R5 | R6 |
|---|---|---|---|---|---|
| Gs | H or CH$_3$ | H | | | |
| I | H or CH$_3$ | | H | | |
| U | | | | H or CH$_3$ | |
| U2s | | | | H or CH$_3$ | |
| U4s | | | | H or CH$_3$ | |
| C | | | | H or CH$_3$ | H |
| Py-2o | | | H or CH$_3$ | H or CH$_3$ | |
| Cs | | | | H or CH$_3$ | H |
| isoG | H or CH$_3$ | H | | | |
| isoGs | H or CH$_3$ | H | | | |
| Pu-2o | H or CH$_3$ | | H | | |
| isoC | | H | | H or CH$_3$ | |
| isoCs | | H | | H or CH$_3$ | |
| Py-4o | | | H or CH$_3$ | H or CH$_3$ | |
| A | H or CH$_3$ | H | CH$_3$ | | |
| isoA | H or CH$_3$ | H | CH$_3$ | | |
| D | H or CH$_3$ | CH$_3$ | | | |
| G | H or CH$_3$ | CH$_3$ | | | |
| Gs | H or CH$_3$ | CH$_3$ | | | |
| I | H or CH$_3$ | | CH$_3$ | | |
| U | | | | H or CH$_3$ | |
| U2s | | | | H or CH$_3$ | |
| U4s | | | | H or CH$_3$ | |
| C | | | | H or CH$_3$ | CH$_3$ |
| Py-2o | | | H or CH$_3$ | H or CH$_3$ | |
| Cs | | | | H or CH$_3$ | CH$_3$ |
| isoG | H or CH$_3$ | CH$_3$ | | | |
| isoGs | H or CH$_3$ | CH$_3$ | | | |
| Pu-2o | H or CH$_3$ | | CH$_3$ | | |
| isoC | | CH$_3$ | | CH$_3$ or CH$_3$ | |
| isoCs | | CH$_3$ | | CH$_3$ or CH$_3$ | |
| Py-4o | | | H or CH$_3$ | H or CH$_3$ | |

In other examples, one or more of the H or CH$_3$ are independently substituted with a halogen such as Cl or F. Examples of further bases and base-pairs compatible with the invention are depicted in FIG. 9. R$_1$ or "BB" in the structures of FIGS. 6 and 9 may serve as a point of attachment to a backbone group, such as PNA, DNA, RNA, etc.

Figure 2A:
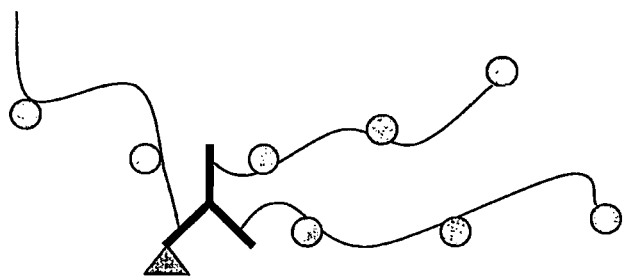
FIG. 2 depicts exemplary linker derivatives which may be employed to detect proteins or nucleic acid targets in a system. Panel A shows an antibody (depicted by an upside-down Y) conjugated to three linker derivatives, each comprising multiple fluorophores (shaded circles). The multiple fluorophores may be used to detect binding between the antibody and an antigen (shaded triangle). Panel B shows an exemplary linker derivative comprising PNA (thick line) and multiple fluorophores (shaded circles), which recognizes a target nucleic acid sequence.
Figure 2B:
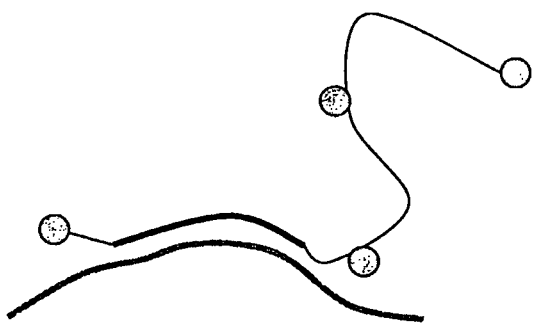

In some embodiments, the following types of base pairs are used: one or more of Us:A, T:D, C:G, and P:Gs. In some embodiments, T:A and P:G are used. Still other examples are illustrated in FIGS. 2(A) and 2(B) of Buchardt et al. (U.S. Pat. No. 6,357,163).

Nucleic acid analogs may also comprise monomer units in which natural bases A, C, G, T, and U or non-natural bases are connected to a non-natural backbone unit. Non-natural backbone units include, for example, those with a backbone other than ribose-phosphate or deoxyribose-phosphate. For example, in some embodiments, one or more phosphate oxygens may be replaced by another molecule, such as sulfur. In other embodiments, a different sugar or a sugar analog may be used, for example, one in which a sugar oxygen is replaced by hydrogen or an amine, or an O-methyl. In yet other embodiments, nucleic acid analogs comprise synthetic molecules that can bind to a nucleic acid or nucleic acid analog. For example, a nucleic acid analog may be comprised of peptide nucleic acids (PNAs), locked nucleic acids (LNAs), or any derivatized form of a nucleic acid.

As used herein, "peptide nucleic acid" or "PNA" means any oligomer or polymer comprising at least one or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163; all of which are herein incorporated by reference.

The term PNA also applies to any oligomer or polymer segment comprising one or more subunits of the nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62: 5441-5450 (1997); Altmann, K- H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, *Eur. J. Biochem.*, 270:1628-44 (2003).

5. Linker Derivatives Comprising Fluorophores

In some embodiments, linkers may be conjugated to one or more fluorophores. For example, two fluorophores may be conjugated to form a fluorophore-linker-Lys(fluorophore)-linker-X derivative. Similarly, one may prepare longer derivatives in which several fluorophores are spaced in between linker units of the same or varying lengths, such as in a Fluorophore-[linker-Lys(fluorophore)]$_N$-linker-X construct, in which X is a conjugating group, or another atom, group, or molecule. In some embodiments, two fluorophores are separated from each other by at least four L15 units (L90) in order to ensure that the fluorophores are separated beyond the Foerster Radius (typically not more than 5 nm) such that quenching due to fluorescence resonance energy transfer is minimized or eliminated. In some embodiments, two fluorophores may be separated by four to ten L15 units (L90 to L150), while in others, by four to six L15 units (L90 to L120). In fact, in some embodiments, fluoresceins spaced by at least four L15 units (L90) showed negligible quenching in aqueous buffers, strongly indicating that the linker adopts an extended structure in water. In contrast, polyethylene glycol (PEG)-based spacers may adopt a collapsed, coiled structure in water.

Because the linkers of the present invention may allow for the separation of individual fluorophores such that quenching is minimized, two or more different types of fluorophores may be conjugated to one or more linkers to produce amplified or uniquely colored signals. For example, 2, 3, 4, or 5 fluorophore groups may be conjugated to linkers, each spaced at least four L15 units apart, for example, spaced between four and ten L15 units or four and six L15 units apart. Some embodiments of this invention comprise Rhodamine-L-Lys (Fluorescein)-L-X in which L contains a sufficient length to avoid quenching of the rhodamine and fluorescein signals, for example, and in which X is another atom, group, or molecule or a conjugating group. The optimal spacing for a given fluorophore depends in part upon its Size, but may readily be determined by testing the intensity of the fluorescent signal at various spacings, for example.

In some embodiments, a molecule such as a protein may be conjugated to several linker derivatives which are each conjugated to a detectable label such as a fluorophore. (See FIG. 2A) In conventional protein fluorescence labeling methods without linkers or with short linkers, the size of the conjugated protein determines how far apart the attached fluorophores can be placed, and consequently, primarily determines the fluorescence intensity. The same principle applies to other molecules as well. In contrast, embodiments of the present invention may relieve this size constraint because the instant linkers can: (1) conjugate to several fluorophores, (2) maintain an extended structure in solution that minimizes unwanted interactions between the individual fluorophores, and (3) conjugate to many types of proteins and other molecules. Thus, in some embodiments, this invention may greatly enhance the fluorescence intensity of a molecule, and may eliminate the need for the extra steps commonly employed to enhance a signal in a system. For example, attaching multiple linker derivatives each comprising multiple fluorophores to an antibody may allow for direct detection of minute quantities of an antigen without the need for secondary antibody signal-amplification procedures.

6. Linker Derivatives with Multiple Conjugated Substances

Some linker derivatives according to this invention include different types of conjugated detectable labels. In some embodiments, linkers are conjugated to two different detectable labels in which one label serves to monitor a change or event in a system by binding to or hybridizing with a target, while the other serves to detect that binding event via a color change, radioactivity, or some other detectable signal. For example, a fluorophore may be combined with a different type of color label. Derivatives such as DNP-linker-Lys(Fluorophore)-linker-X have been prepared. DNP (dinitrophenol) may be recognized, by an anti-DNP antibody while the fluorescent emission provides a second type of signal, thus providing two alternative labeling methods.

Further, embodiments of the present invention may comprise other combinations of atoms, groups, or molecules such as a detectable label and a solid surface, membrane, protein, or other large molecule. Attachments may be covalent as well as non-covalent. Embodiments with more than one type of conjugated atom, group, or molecule are useful, for example, in immunoprecipitation or ELIZA assays, in situ detection assays, multi-layer assays, fluorescent micro-sphere assays, and capture assays.

In some embodiments, linkers are conjugated to fluorophores as well as to probes such as nucleic acids and nucleic acid analogs. For example, a nucleic acid or nucleic acid analog may be used to hybridize to a target sequence in a system, while the fluorophore conjugated to the probe through the linker provides a means to detect the hybridization. Such bifunctionally labeled linker derivatives may be useful, for example, in in situ hybridization assays such as FISH.

Other linker derivatives according to this invention comprise multiple nucleic acid or nucleic acid analog conjugates, optionally further conjugated with other types of detectable labels. For example, a single linker derivative molecule may comprise several different nucleic acid or nucleic acid analogs, each separated from the others by stretches of one or more L15 units. In some embodiments, the different nucleic acid or nucleic acid analogs are separated from each other by spacings of L120 to L300, L150 to L300, or L300.

In some embodiments, linkers are conjugated to fluorophores or other color-based labels as well as to PNA or LNA probes. PNA-containing linker derivatives made according to the present invention include, for example, X-L-PNA-L-Lys (Cys) comprising linker derivatives, in which X may be an end-group such as acetyl, a conjugating group, or a color label such as a fluorophore or enzyme substrate such as DNP. Attachment of a fluorophore such as fluorescein may allow simpler purification and analysis of the derivative. A spacing of L30 or larger between the X group and a PNA or oligonucleotide is generally a sufficient distance to avoid steric hindrance between the linker and the hybridization target, however longer spacing may be used, for example to increase entropy to further minimize unwanted tertiary interactions or aggregation. For instance, the distance between the PNA or oligonucleotide and a Lys(Cys) group may be, for example, up to L300, including from L120 to L300 or from L150 to L300. Spacings between the PNA and other conjugates may be, for example, from L120 to L300, from L150 to L300, or L300. Other exemplary PNA-comprising linker derivatives according to the invention also include multiple fluorophore or color label attachments. For example, the derivative [Flu-L60)$_2$Lys-]$_2$Lys-L30-PNA was prepared and contains four fluorescein linker derivatives (Flu). In other embodiments, a linear linker derivative may be prepared, conjugated to PNA and multiple fluorophores. The embodiment Lys(Flu)-L30-PNA-L30-Lys(Flu)-L90-Lys(Flu)-L90-Lys(Flu) was also prepared and similarly contains four fluoresceins. While fluorophores conjugated to the same linker derivative can be more likely to aggregate in solution than fluorophores conjugated to different linker derivatives, surprisingly, linker derivatives comprising a PNA probe and several fluorophores spaced by L90 linkers not only gave enhanced signals over others containing single fluorophores, but also showed a reduced background, indicating that the high entropy due to the flexible, extended structure of each L90 linker more than compensated for any increased tendency for the fluorophores to interact. In some embodiments, the linker derivatives may also form branched structures or may specifically hybridize with each other via the conjugated PNAs so as to amplify the signal.

7. Cross-Linking Agents

The linkers of the present invention may also be used as protein cross-linkers. For example, the instant linkers may be conjugated with a protein conjugating group such as malemide, and/or with an antigen, ligand, or substrate for a particular protein or antibody, and optionally also with a detectable label in order to visualize the cross-link. For instance, malemide-linker-X groups have been prepared, in which X represents a reactive group such as Lys(betaalanine-N,N diacetic acid), or a specific ligand, antigen, or substrate of the protein of interest. Such a linker can be used, for example, to bind to a specific protein or antibody via the X group, and to cross link to other proteins in the vicinity of that specific protein via the malemide-linker. A detectable label may also be conjugated to the linker derivative to aid in detecting the cross-link. Even relatively short linker segments such as L30 between a label and a protein ligand may allow for detection of the label without significant interference from quenching of a fluorescent label, for example.

The extended, flexible structure of some of the instant linkers allows them to assist in the cross-linking of even two large molecules, such as a fluorescent protein (for example, RPE or green fluorescent protein) and an antibody. For example, long linkers according to the present invention may have lengths in solution of, for instance, 9 nm in the case of L90, or even 30 nm in the case of L300, or even longer. That length provides significant freedom for even very large proteins within a cross-linked complex to adopt their preferred orientations independently of others within the complex. Thus, the instant linkers allow for more accurate identification of interacting proteins because the complex is minimally perturbed by the presence of the linker.

Surface or Polymer Conjugation

Figure 3:
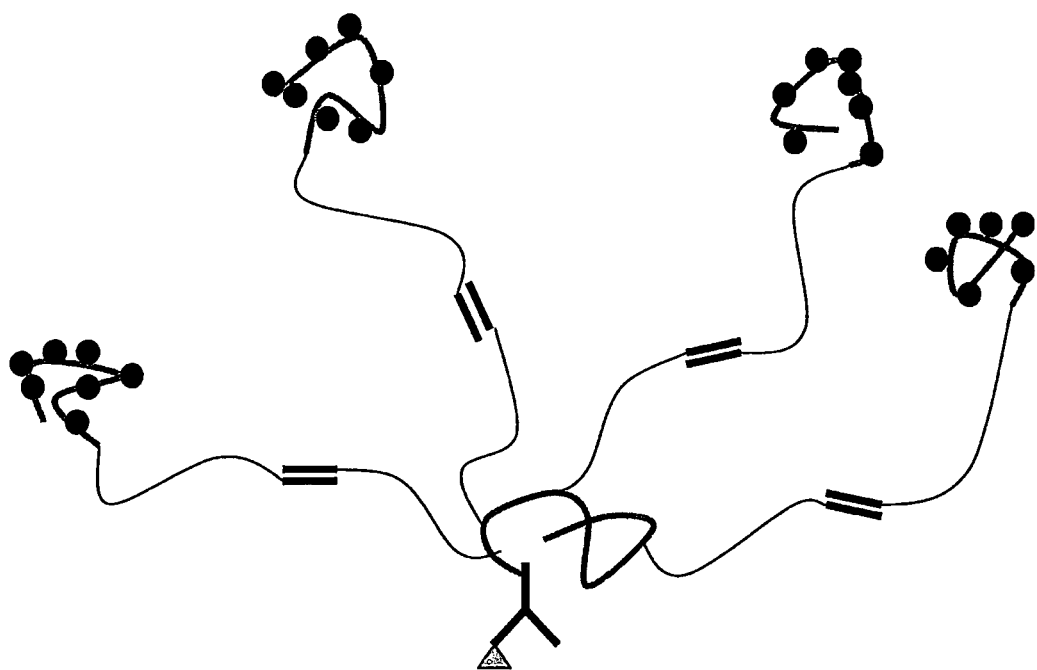
FIG. 3 depicts an exemplary multi-layer assay. Binding between an antibody (upside down Y) and an antigen (shaded triangle) may be detected by first conjugating the antibody directly or indirectly to a first linker derivative comprising a nucleic acid or nucleic acid analog sequence, then conjugating the first linker derivative to a second linker derivative which is conjugated to both dextran and a complementary nucleic acid or nucleic acid analog sequence. Hybridization between the two nucleic acid or nucleic acid sequences is depicted by the parallel bars at the center of the drawing. Dextran beads are shown as dark circles at the top of the drawing.

In some embodiments, the instant linkers may serve to covalently or non-covalently attach a detectable label or other atom, group, or molecule to a polymer or a surface such as dextran or a membrane or an array or a plate. The instant linkers take up little space in the longitudinal direction. Hence, they may be useful in coating such surfaces at high density because they can access relatively narrow spaces or pores in such surfaces. Further, long linkers may be employed in order to maximize the distance between the surface and other components of the system, such that the system is minimally perturbed. For example, linker derivatives can be prepared for conjugation to dextran in conjunction with nucleic acids or nucleic acid analogs such as PNA as well as color labels such as HRP and one or more fluorophores. Other linker derivatives can be prepared for conjugation to combinations of dextran, PNA, and antibodies. (See FIG. 3, for example.)

Linker derivatives with multiple conjugated atoms, groups, or molecules may be used to amplify signals in a variety of ways. For example, minute quantities of antibodies or antigens may be detected by attaching the antibody or antigen to a linker derivative comprising multiple fluorophores. (See FIG. 2A, for example.) {Note: this was already discussed above.} Further, two potentially cross-reactive antigens may be distinguished by attaching the antigens to linker derivatives comprising different types of fluorophores. Multi-layer systems may also be constructed in which certain interacting atoms, groups, or molecules such as complementary nucleic acids or nucleic acid analogs or a protein and a ligand are placed in between another detectable label such as a color label and a surface or molecule. (See FIG. 3.)

9. Enhancing the Solubility of Conjugated Substances

Another surprising feature of some of the instant linkers is a relatively high solubility despite the presence of relatively few polar or charged groups. Hence, linkers, for example, those comprising two or more L15 units in some derivatives, or four or more L15 units in other derivatives, may also be employed to enhance the solubility of an atom, group, or molecule in aqueous solution. For example, an acetyl-L-X group may be used to enhance the solubility of the atom, group, or molecule X. Surprisingly, PNA probes with multiple fluorophores spaced via at least four L15 units showed higher water solubility, as well as less aggregation and less non-specific binding, than those without conjugated linkers and with only one fluorophore. Further, poly-linker derivatives of the present invention conjugated to even 50 to 100 bases of PNA as well as to fluorophores did not aggregate and showed high water solubility. {Note: no need to include the extra information regarding lack of "stickiness" in the application itself. We can introduce it in prosecution if needed.}

10. Other Exemplary Uses of Linker Derivatives

In yet other embodiments, the instant linkers, may be conjugated to a drug compound, for instance, to increase its retention, solubility, or to effectively link it to another group so as to target it to a particular area of the body. For example, in some embodiments, at least one linker of homogeneous molecular and structural formula is conjugated to at least one drug compound.

The instant linkers are also useful in a variety of biological and chemical assays. For instance, in capture assays, steric barriers may be relieved by in effect lifting a probe from a surface so that it is free in solution to recognize its target. (See FIG. 5.) If the rate of binding between the probe and target is slow relative to the rate of diffusion, a shorter linker length may be employed. However, when the rate of binding is rapid compared to the rate of diffusion in the system, a long linker may be advantageous. Because the instant linkers may be prepared at precise short or long lengths, as well as in mixtures of different lengths, depending on the synthesis method used, the instant linkers provide a uniform system around which such assays may be designed.

The present invention is further illustrated by the following non-limiting examples.

EXAMPLES

Example 1

Synthesis of L30 and L60 Linkers

Part A:

A solution of 146 mL 2,2'-(Ethylenedioxy)bis(ethylamine) (98%) in 360 mL tetrahydrofuran (THF) was cooled on an ice bath. To this a solution of 65 g Di-tert-butyl dicarbonate (97%) in 260 mL THF was added drop-wise over 1 h. The solvent was evaporated on a rotary evaporator. The product was washed with 300 mL of water and the solvent was again removed.

The product was taken up in 300 mL water and was extracted with 300 mL dichloromethane (DCM), then further extracted with 2×150 mL DCM. The collected organic phase was washed with 50 mL water before evaporating to about half the volume.

The DCM was then extracted with 400 mL 1M solution of NaCitrate (pH 4.5), then further extracted with another 50 mL of the NaCitrate solution. The two resulting aqueous phases were washed with 50 mL DCM before cooling on an ice bath. Under stirring 100 mL NaOH 10 M was added until the pH of the solution was >13.

In a separation funnel the product separated on its own. It was shaken with 300 mL DCM and 50 ml water. The organic phase was then evaporated, giving a white oil.

Yield 48.9 g=65.7%. $C_{11}H_{24}N_2O_4$ MS calc. 248.3. found 248.5. (See structure 1, FIG. 1.)

Part B: Preparation of Boc-L15-Imide 76.2 g of structure 1 (FIG. 1), prepared, for example, as described in part A above, was dissolved in 155 mL pyridine. 54.0 g diglycolic anhydride (90%) was added and the solution was stirred for 15 min. Next, 117 mL acetic anhydride (min. 98%) was added and stirring continued at 95° C. for 1 h. The solvents were evaporated on rotary evaporator.

117 mL water was added and the solution stirred for 15 min's before further 272 mL water and 193 mL DCM was added. The organic layer was extracted twice with 193 mL $Na_2CO_3$ (1 M) and then twice with a mixture of 72 mL HCl 4 M and 289 mL of 1M sodium citrate, pH 4.5. After each extraction the aqueous phase was washed with a little DCM. The collected organic phase was washed with 150 mL of water. The solvent was evaporated leaving the product (structure 2 of FIG. 1) as a pale oil.

Yield 100.3 g (0.29 mol)=94%. $C_{13}H_{26}N_2O_7$ MS calc. 346.4. found 346.7.

Part C:

100.3 g structure 2 (FIG. 1) was dissolved in 100 mL THF and added drop-wise to 169.4 mL of 2,2'-(Ethylendioxy)bis (ethylamine) at 60° C. over 1 h. The amine was distilled from the reaction mixture at 75-80° C./0.3 mBar.

The residue from the distillation was taken up in a mixture of 88 mL HCl 4 M and 350 mL 1M NaCitrate, pH 4.5 and extracted three times with 175 mL DCM. The aqueous phase was cooled in an ice bath and 105 mL of 10 M NaOH was added.

In a separation funnel the product slowly separated from the solution. When separated, the product was partitioned between 100 mL of water and 950 mL of DCM. The aqueous phase was further extracted four times with 150 mL of DCM and the combined DCM phases reduced to an oil. The oily residue was dehydrated by evaporation from toluene, giving a yellow oil.

Yield 115.48 g=81%. $C_{21}H_{42}N_4O_9$ MS calc. 494.6. found 494.8. (See structure 3, FIG. 1.)

Part D: Preparation of Boc-L30-Imide 115.5 g of structure 3 (FIG. 1) was dissolved in 115 mL pyridine. 40.6 g diglycolic anhydride (90%) was added. After stirring for 15 min, 97 mL acetic anhydride (min. 98%) was added, and the solution was stirred at 95° C. for 1 h. The solvent was evaporated under reduced pressure.

The reaction mixture was cooled a little and 80 mL of water was added. The reaction mixture was stirred for 15 min, then 200 mL water and 150 mL DCM were added. The organic layer was extracted twice with 150 mL $Na_2CO_3$ (1 M) and then twice with a mixture of 53 mL HCl (4 M) and 213 mL of NaCitrate (1 M). After each extraction, the aqueous phase was washed with a little DCM.

The collected organic phase was washed with 150 mL of water. The solvent was evaporated. The oily residue was dehydrated by evaporation from toluene, giving a yellow oil.

Yield 125 g=92%. $C_{25}H_{44}N_4O_{12}$ MS calc. 592.6. found 592.5. (See structure 4 of FIG. 1.)

Further purifying of the product is performed on a silica column with a gradient from 5-10% methanol in DCM. Alternatively, the product is used for further chemical reactions. Yield 69% white oil.

Part E: Ring Opening to Prepare Boc-L30 Free Acid 12.4 g of structure 4 (FIG. 1) was dissolved in 12 mL water, 12 mL 1,4-dioxane and 6 mL DIPEA and refluxed for 30 min, then cooled and evaporated. The oily residue was dehydrated by evaporation from toluene, giving a yellow oil. $C_{25}H_{46}N_4O_{14}$ MS calc. 610.6. found 610.8. (See structure 5, FIG. 1.)

Part F: Preparation of an L-60 Linker from Boc-L30-Imide

To prepare a Boc-L60-imide from two shorter linkers, Boc-L30-imide, 10 g, was dissolved in 100 mL of trifluoroacetic acid (TFA). After 10 min the TFA was evaporated off under reduced pressure to leave 20 g off free amine-L30-imide: TFA adduct. This was dissolved in 100 mL of acetonitrile and neutralized with 15 mL triethyl amine.

To this solution was added 10.3 g Boc-L30-free acid activated with 6.2 g HATU (N-[(dimethylamino)-1H-1,2,3-triazolo [4,5-b]pyridi-1-ylmethylene]-N-methylmethaneaminium hexafluorophosphate N-oxide) and diisopropylethyl amine 4.5 mL in 50 mL acetonitrile for 5 min.

After 1 hour the solvents were evaporated off, the product taken up in 500 mL dichloromethane and extracted with 150 mL 1 M sodium carbonate. The dichloromethane was evaporated off and the product purified on silica with 15% methanol in dichloromethane. Yield: 12.3 g of Boc-L60-imide, or 67%.

To prepare Boc-L60 free acid, 12.3 g Boc-L60-imide was dissolved in 20 mL water; 20 mL dioxane and 20 mL diisopropylethyl amine and boiled for 1 h. The solvents were evaporated off to leave 14.3 g of Boc-L60-free acid diisopropyl ethyl amine salt. A TLC analysis showed that the reaction was quantitative.

Example 2

Synthesis of Longer Linkers and Linker Derivatives—General Procedures

Longer linker derivatives were prepared by solid phase syntheses. Initially the resin was "downloaded" for solid phase syntheses. As many linker derivatives reach molecular weights of, for example, 10 kDa, a corresponding amount of resin should be downloaded. For example, as a rule of thumb, the loading in mol/g multiplied by the molecular weight of the desired product in g/mol should not exceed 1, corresponding to a formal crude yield of 1 g product/1 g resin.

General procedures for preparation of components of linker derivatives are also described in this example.

Synthesis of Linkers

Resin Downloading Procedure 3 g MBHA-resin (01-64-0042, NovaBiochem) was swelled in NMP (N-Methyl-Pyrolidone) overnight. It was washed with pyridine (2×) then with NMP and drained.

Boc-Lys(Fmoc)-OH (04-12-0063, NovaBiochem) 0.15 mmol/g resin, 0.45 mmol, 211 mg and 0.95 eqi. HATU (GEN076525, Applied Biosystems) 162 mg and 2 equi DIPEA (Diisopropylethylamine, 550043, Aldrich) 156 µL was dissolved in 7 mL NMP, activated for 2 min, and then applied to the resin. The reaction was allowed to proceed for 1 h with gentle shaking. The reaction mixture was drained off and the resin washed repeatedly with NMP. The remaining un-reacted amino groups on the resin were acetylated with NMP/Pyridine/acetic anhydride (2:2:1) for not less than 1 h, and until a qualitative Kaiser test failed to show free amino groups. The resin was then washed repeatedly with NMP followed by repeated DCM washes, and finally dried in vacuum. Referred to as "downloaded resin".

A sample of the resin was deprotected with TFA (TriFluoroAcetic Acid)/mCresole, 19:1 for 2×5 min, washed repeatedly with DCM, and dried in vacuum. This sample was subjected to a quantitative Kaiser test to determine the loading. Result=0.085 mmol amino groups/g resin.

Solid Phase Synthesis Procedure

Standard Boc solid phase synthesis procedures were followed:

First, resin was deprotected with TFA (TriFluoroAcetic Acid)/mCresole, 19:1 for 2×5 min, washed repeatedly with DCM, then NMP, then pyridine. Second, Boc-L30-OH, 0.26M in NMP, was mixed with equal volumes of 0.234 M HATU in NMP and 0.5M DIPEA in pyridine and allowed to activate for 2 min prior to addition to resin. A volume just sufficient to cover the resin was used, and the coupling reaction allowed to proceed for 20 min. Generally a single such coupling would suffice to obtain a negative Kaiser test, however when coupling to an αNH$_2$-Lys(cFmoc) residue, a double coupling was performed.

To avoid traces of deleted products, a capping step with acetic anhydride/NMP/pyridine 2:49:49 for 2 min was used after each coupling. The resin was washed with NMP and then DCM in preparation of the next deprotection step.

Boc-protected amino acids and PNA monomers were introduced using standard conditions. Lysine residues were introduced to allow side chain deprotection on the resin, as well as introduction of for instance fluorophores.

Fmoc-protection groups were removed with piperidine/NMP 1:4 for 2×5 min. Dde and protection groups were removed with 3% hydrazine in NMP for 2×5 min.

Syntheses were also carried out on an ABI 433A peptide synthesizer according to the manufacturer's instructions (Applied Biosystems, Inc., Foster City, Calif.).

In general it was observed that Boc-L30-OH coupled well, especially onto itself. Apart from the mentioned αNH$_2$-Lys (εFmoc) residues, double couplings had to be performed only if preparing a branched structure, with simultaneous coupling onto several free amino terminals of the same compound.

A remarkable feature of resins with longer stretches of linker attached was an extraordinary quelling, especially during deprotection in TFA. For instance, when departing from 1 g of downloaded resin, 3 mL of TFA would easily suffice to quell and cover the resin. However, after 10 Boc-L30-OH couplings (the resin now with Boc-L300 attached), more that 10 mL of TFA was required to quell and cover the resin. On the other hand, it did not appear that even such a Boc-L300 stretch on the αN of a C-terminal Lysine gave rise to any problems when performing chemistry on the ε-N of the Lysine residue. For example, an Fmoc group was readily cleaved from this position, and subsequent couplings to that position appeared to be unaffected by the long linker.

Removal from the Solid Phase Resin

Once the desired product was obtained on the resin, it was cleaved off the resin using TrifluoroMethaneSulphonicAcid/TFA/M-Cresole, 7:2:1, liberating the product as a C-terminal carboxamide. The product was precipitated with diethyl ether and dried in a stream of nitrogen. The crude products were dissolved in 15% acetonitrile in water, and purification was performed by RP-HPLC. A gradient of 15% to 40% acetonitrile in 0.02% aqueous TFA was typically used. It was observed that longer linker derivatives were slightly acid labile. Prior to freeze-drying, the HPLC elution buffer was typically neutralized with an appropriate base such as MES (2-[N-Morpholino]ethanesulphoninc acid) sodium salt. For instance, a product isolated in 5 mL 0.02% TFA contains 1 µl TFA, or 12 µmol, and was neutralized to pH 6 with 25 µL 1 M MES sodium salt. This procedure was used for linker derivatives that were later to be used in water. Pyridine or DIPEA was used for neutralization when the products were to be used in an organic solvent, or where inorganic salts would have presented a solubility problem in aqueous solutions.

Solid Phase PNA Synthesis

On a peptide synthesizer (ABI 433A, Applied Biosystems) PNA monomers are coupled to the resin using standard procedures for amino acid coupling and standard PNA chemistry. Then the resin is handled in a glass vial to remove protections groups and to label with either other amino acids or flourophores.

Removal of the indicated protection groups is achieved with the following conditions:

Boc: TFA/m-cresol (at a ratio of 95/5) 2×5 min.
Fmoc: 20% piperidine in DMF 2×5 min.
Ode: 3% hydrazine in DMF 2×5 min. with TFA/TFMSA/m-cresol/thioanisol (at a ratio of 6/2/1/1). The PNA is then precipitated with ether and purified on HPLC. MALDI-TOF mass spectrometry is used to determine the molecular weight of the product. {NOTE—this is from the Funny Bases Example 2.}

Preparation of Non-Natural Bases and PNA Monomers

Pyrimidinone-Monomer (Method 1)

1. In dry equipment 4.6 g of solid Na in small pieces was added to 400 mL ethanol (99.9%), and was dissolved by stirring. Hydroxypyrimidine hydrochloride, 13.2 g, was added and the mixture refluxed for 10 minutes. Then 12.2 mL ethyl-bromoacetate (98%) was added and the mixture refluxed for 1½ hour. The reaction was followed using Thin Layer Chromatography (TLC). The ethanol was evaporated leaving a white compound, which was dissolved in a mixture of 80 mL of 1M NaCitrate (pH 4.5) and 40 mL of 2M NaOH. This solution was extracted four times with 100 mL Dichloromethane (DCM). The DCM phases were pooled and washed with 10 mL NaCitrate/NaOH—mixture. The washed DCM phases were evaporated under reduced pressure and resulted in 17.2 g of crude solid product. This crude solid product was recrystallized with ethylacetate giving a yellow powder. The yield for this step was 11.45 g (63%).

2. The yellow powder, 12.45 g. from above was hydrolyzed by refluxing overnight in a mixture of 36 mL DIPEA, 72 mL water and 72 mL dioxane. The solvent was evaporated and water was removed from the residue by evaporation from toluene. The yield for this step was 100%.

3. OBS. Pyrimidinone acetic acid (10.5 g), 16.8 g PNA-backbone ethylester, 12.3 g DHBT-OH, 19 mL Triethylamine was dissolved in 50 mL N,N-dimethylformamide (DMF). DIPIDIC (11.8 mL) was added and the mixture stirred overnight at room temperature. The product was taken up in 100 mL DCM and extracted three times with 100 mL of dilute aqueous NaHCO$_3$. The organic phase was extracted twice with a mixture of 80 mL of 1M NaCitrate and 20 mL of 4M HCl. Because TLC showed that some material was in the citrate phase, it was extracted twice with DCM. The organic phases were pooled and evaporated. Because there was a precipitation of urea, the product was dissolved in a DCM, and the urea filtered off. Subsequent evaporation left an orange oil. Purification of the orange oil was performed on a silica column with 10% methanol in DCM. The fractions were collected and evaporated giving a yellow foam. The yield for this step was 7.0 g (26.8%).

4. The yellow foam (8.0 g) was hydrolyzed by reflux overnight in 11 mL DIPEA, 22 mL water, and 22 mL dioxane. The solvent was evaporated and the oil was dehydrated by evaporation from toluene leaving an orange foam. The yield for this step was 100%.

Pyrimidinone-Monomer (Method 2)

Step 1. In dry equipment 9.2 g of solid Na in small pieces was dissolved in 400 mL ethanol (99.9%), with stirring. Hydroxypyrimidine hydrochlorid, 26.5 g, was added, and the mixture was stirred for 10 minutes at 50° C. Then 24.4 mL Ethyl bromoacetate (98%) was added and the mixture stirred at 50° C. for 1 hour. The reaction was followed using Thin Layer Chromatography (TLC).

The ethanol was evaporated leaving a white compound, which was dissolved in 70 mL of water and extracted with 20 mL DCM. Another 30 mL of water was added to the water phase, which was extracted with 3×100 mL DCM. The DCM-phase from the first extraction contains a lot of product, but also some impurities, wherefore this phase was extracted twice with water. These two water phases then were back extracted with DCM.

The combined DCM phases were pooled and washed with 10 mL water. The washed DCM phases were evaporation under reduced pressure and resulted in 25.1 g yellow powder. The yield for this step was 25.1 g=69%. Maldi-Tof: 181.7 (calc. 182).

Step 2. 34.86 g yellow powder from above was dissolved in 144 mL 2M NaOH. After stirring 10 minutes at room temperature, the mixture was cooled in an ice bath. Now 72 mL 4 M HCl (cold) was added. The product precipitated. After stirring for 5 minutes, the precipitate was filtered and thoroughly washed with ice water. Drying in a dessicator under reduced pressure left 18.98 g yellow powder. The yield for this step was 18.98 g=64%.

Step 3. Pyrimidinone acetic acid 11.1 g and triethylamine 12.5 mL were dissolved in N,N-dimethylformamide (DMF) 24 ml, HBTU 26.2 g was added plus 6 mL extra DMF. After 2 minutes a solution of PNA-Backbone ethylester 14.7 g dissolved in 15 mL DMF was added. The reaction mixture was stirred at room temperature and followed using TLC. After ½ hour precipitate had formed. This was filtered off.

The product was taken up in 100 mL DCM and extracted with 2×100 mL dilute aqueous NaHCO3. Both of the aqueous phases were washed with a little DCM. The organic phases were pooled and evaporated. Evaporation left an orange oil. Purification of the product was done on a silica column with 10-20% methanol in'ethylacetate. The fractions were collected and evaporated giving a yellow oil. The oil was dissolved and evaporated twice from ethanol. The yield from this step was 20.68 g=90%.

Step 4. The yellow oil (18.75 g) was dissolved in 368 mL 0.2 M Ba(OH)2. Stirring for 10 minutes before 333 mL 0.221 M H2SO4 was added. A precipitation was performed immediately. Filtration through cellite, which was washed with water. The solvent was evaporated. Before the evaporation was at end, the product was centrifuged to get rid of the very rest of the precipitation. Re-evaporation of the solvent left a yellow oil. The yield from this step was 13.56 g=78%.

Step 5. To make a test on the P-monomer 3 consecutive P's were coupled to Boc-L300-Lys(Fmoc)-resin, following normal PNA standard procedure. The product was cleaved from the resin and precipitated also following standard procedures: HPPP-L300-Lys(Fmoc). Maldi-Tof on the crude product: 6000 (calc. 6000) showing only minor impurities.

Thio-Guanine Monomer 1. 6-Chloroguanine (4.93 g) and 10.05 g $K_2CO_3$ was stirred with 40 mL DMF for 10 minutes at room temperature. The reaction mixture was placed in a water bath at room temperature and 3.55 mL ethyl bromoacetate was added. The mixture was stirred in a water bath until TLC (20% Methanol/DCM) showed that the reaction was finished. The precipitated carbonate was filtered off and washed twice with 10 mL DMF. The solution, which was a little cloudy, was added to 300 ml water, whereby it became clear. On an ice bath the target compound slowly precipitated. After filtration the crystals were washed with cold ethanol and dried in a desiccator. The yield for this step was 3.3 g (44.3%) of ethyl chloroguanine acetate.

2. Ethyl chloroguanine acetate (3.3 g) was dissolved by reflux in 50 mL absolute ethanol. Thiourea (1.08 g) was added. After a refluxing for a short time, precipitate slowly began forming. According to TLC (20% Methanol/DCM) the reaction was finished in 45 minutes. Upon completion, the mixture was cooled on an ice bath. The precipitate was then filtered and dried overnight in a desiccator. The yield for this step was 2.0 g (60%) ethyl thioguanine acetate.

3. Ethyl thioguanine acetate (3.57 g) was dissolved in 42 mL DMF. Benzylbromide (2.46 mL) was then added and the mixture stirred in an oil bath at 45° C. The reaction was followed using TLC (25% Methanol/DCM). After 3 hours all basis material was consumed. The step 3 target compound precipitated upon evaporation under reduced pressure and high temperature. The precipitate was recrystallized in absolute ethanol, filtered and then dried in a desiccator. The yield for this step was 3.88 g (82%) of methyl benzyl thioguanine ethylester.

4. Methyl benzyl thioguanine ethylester (5.68 g) was dissolved in 12.4 mL of 2M NaOH and 40 mL THF, and then stirred for 10 minutes. The THF was evaporated by. This was repeated. The material was dissolved in water and then 6.2 mL of 4M HCl was added, whereby the target product precipitated. Filtering and drying in a desiccator. The yield for this step was 4.02 g (77%).

5. The product of step 4 (4.02 g), 3.45 g backbone ethylester, 9 mL DMF, 3 mL pyridine, 2.1 mL triethylamine and 7.28 g PyBop were mixed and then stirred at room temperature. After 90 minutes a solid precipitation formed. The product was taken up in 125 mL DCM and 25 mL methanol. This solution was then extracted, first with a mixture of 80 mL of 1 M NaCitrate and 20 mL of 4M HCl, and then with 100 mL dilute aqueous $NaHCO_3$. Evaporation of the organic phase gave a solid material. The material was dissolved in 175 mL boiling ethanol. The volume of the solution was reduced to about 100 mL by boiling. Upon cooling in an ice bath, the target product precipitate. The crystals were filtered, washed with cold ethanol and then dried in a desiccator. The yield of this step was 6.0 g (86%.)

6. The product of step 5 (6.0 g) was dissolved in 80 mL THF, 7.5 mL 2M NaOH and 25 mL water. The solution became clear after ten minutes of stirring. THF was evaporated. Water (50 mL) was added to the mixture. THF was evaporated. Water (50 mL) was added to the mixture. When the pH was adjusted by the addition of 3.75 mL of 4M HCl, thio-guanine monomer precipitated. It was then filtered, washed with water and dried in a desiccator. The yield for this step was 5.15 g (91%).

Diaminopurine Acetic Acid Ethyl Ester

1. Diaminopurine (10 g) and 40 g of $K_2CO_3$ were added to 85 mL of DMF and stirred for 30 minutes. The mixture was cooled in a water bath to 15° C. Ethyl bromoacetate (3 mL) was added three times with 20 minute intervals between each addition. This mixture was then stirred for 20 minutes at 15° C. The mixture was left in the water bath for another 75 minutes, and the temperature increased to 18° C. The DMF was removed by filtering and the remaining $K_2CO_3$ was added to 100 mL of ethanol and refluxed for 5 minutes. Filtering and repeated reflux of the $K_2CO_3$ in 50 mL ethanol, filtering. The pooled ethanol phases were placed in a freezer, after which crystals formed. These crystals were filtered, washed with cold ethanol, filtered again and then dried in a desiccator overnight. The yield for this step was 12 g (76%).

Other General Procedures

Amino Acid Coupling

The Boc protection group is removed from the resin with TFA/m-cresol (at a ratio of 95/5) 2×5 min. The resin is then washed with DCM, pyridine and DMF before coupling with the amino acid, which is dissolved in NMP in a concentration between 0.2 and 0.4 M and activated with 0.95 eq. of HATU and 2 eq of DIPEA for 2 minutes. The coupling is complete when the Kaiser test is negative. Capping occurring by exposing the resin for 3 minutes to $(Ac)_2O$/pyridine/NMP (at a ratio of 1/2/2). The resin is then washed with DMF and DCM.

Boc-$L_{300}$-Lys(Fmoc)-Resin

To the loaded Boc-Lys(Fmoc)-resin, $L_{30}$-Linker in a concentration of 026 M was coupled using standard amino acid coupling. This was done 10 times giving Boc-$L_{300}$-Lys(Fmoc)-resin.

Labeling with Fluorescein

5(6)-carboxy fluorescein is dissolved in NMP to a concentration of 0.2 M. Activation is performed with 0.9 eq. HATU and 1 eq. DIPEA for 2 min before coupling for at least 2×20 min or until the Kaiser test is negative.

Synthesis of Fmoc-L30

Fmoc-L30 is suitable for preparing conjugates with acid-labile substituents. 23 g Boc-L30-acid was dissolved in 200 mL TFA and nitrogen bubbled through the solution for 15 min. TFA was removed as far as possible on rotary evaporator leaving 43 g, (approx. 19 g L30 amino-acid, 24 g TFA). 130 mL acetonitrile was added, and then 42 mL triethylamine (1.5 equivalents relative to residual TFA). The mixture was cooled to room temperature and 16 g of Fmoc-NHS ester added. After 30 min the reaction was complete, and the solvents again evaporated as far as possible. The residue was taken up in 300 mL DCM and 200 mL water in a separating funnel. With 2 M NaOH the pH of the emulsion was carefully adjusted to approx. 8, and very, very slowly a clear aqueous phase formed above the emulsion. After several hours the aqueous phase was collected, and the remaining emulsion again extracted with 200 mL of water, again adding a little extra NaOH till pH 8. Again a slow separation followed and the combined aqueous phases were collected. They were again placed in a separating funnel together with 300 mL DCM, and with 4 M HCl the pH of the aqueous phase adjusted to 3. After some time a clear DCM solution with the product separated off, and the aqueous phase was extracted with with further 200 mL DCM. The combined DCM phases were evaporated to dryness, to give 16 g of Fmoc-L30-acid.

Nomenclature of Representative Products

A strict peptide notion is used to describe the exemplary products below. Thus, the products are all written with the N-terminal to the left, the C-terminal to the right, an "H" to the extreme left denoting a free amino terminal, a "NH$_2$" to the extreme right denoting a C-terminal carboxamide. When lysine residues are substituted on the side chain amino group, this is denoted by putting the substituent in brackets, (NH$_2$) denoting a free amino group; (Flu) 5/6-carboxyfluorescein; (Cys) cysteine, (betaala) beta-alanine-N,N-di acetic acid. PNA residues are denoted in the following way: A=adenine; C=cytosine; D=diaminopurine; G=guanine; Gs=thioguanine; I=inosine; P=2-oxo-pyrimidine (pyrimidinone); T=thymine; U2s=2-thiouracil.

Figure 7:
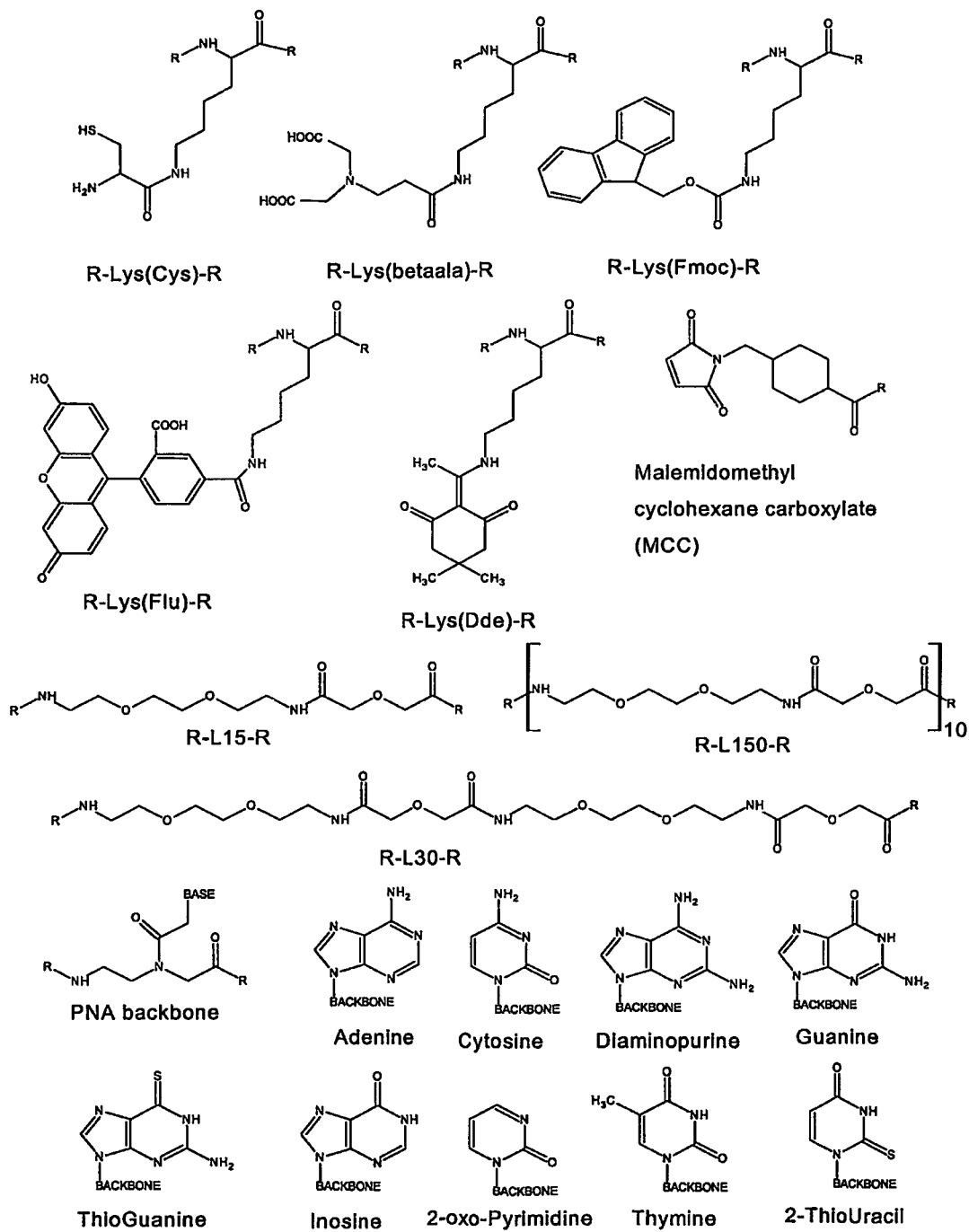
FIG. 7 depicts sample nucleobases, intermediates, and linker derivatives.

FIGS. 6 and 7 depict representative structures of natural and non-natural nucleobases, PNA monomers, intermediates, and linker derivatives.

Example 3

Preparation of Exemplary Linker Derivatives 1-13

1: Ac-L30-Lys(betaala)-NH$_2$.

Downloaded Boc-Lys(Fmoc) resin, 0.5 g, was Fmoc deprotected and subjected to one coupling with beta-alanine-N,N-diacetic acid benzyl ester. The Boc protection group was then removed, and the resin subjected to one coupling with L30. The terminal Boc protected amino group was deprotected and acetylated for 5 min with 2% acetic anhydride in NMP/pyridine. The product was cleaved from the resin, precipitated and purified by RP-HPLC, then neutralized with pyridine and freeze-dried to a colorless oil. Yield was 25 mg. MS calc. for $C_{35}H_{62}N_8O_{17}$ was 866.923.

2: Ac-L60-Lys(betaala)-NH$_2$.

Downloaded Boc-Lys(Fmoc) resin, 0.5 g, was Fmoc deprotected and subjected to one coupling with beta-alanine-N,N-diacetic acid benzyl ester. The Boc protection group was then removed, and the resin subjected to two couplings with L30. The terminal Boc protected amino group was deprotected and acetylated for 5 min with 2% acetic anhydride in NMP/pyridine. The product was cleaved from the resin, precipitated and purified by RP-HPLC, then neutralized with pyridine and freeze-dried to a colorless oil. Yield was 62 mg. MS calc. for $C_{55}H_{98}N_{12}O_{27}$ was 1359.452.

3: Ac-L90-Lys(betaala)-NH$_2$.

Downloaded Boc-Lys(Fmoc) resin, 0.5 g, was Fmoc deprotected and subjected to one coupling with beta-alanine-N,N-diacetic acid benzyl ester. The Boc protection group was then removed, and the resin subjected to 3 couplings with L30. The terminal Boc protected amino group was deprotected and acetylated for 5 min with 2% acetic anhydride in NMP/pyridine. The product was cleaved from the resin, precipitated and purified by RP-HPLC neutralized with pyridine and freeze dried to a colorless oil. Yield was 90 mg. MS calc. for $C_{75}H_{134}N_{16}O_{37}$ was 1851.980.

4: MCC-L150-Lys(betaala)-NH$_2$

Downloaded Boc-L150-Lys(Fmoc) resin, 0.25 g, was Fmoc deprotected and subjected to one coupling with beta-alanine-N,N-diacetic acid benzyl ester. The Boc protection group was then removed, and the product was cleaved from the resin, and precipitated. The crude product was resuspended in 1 mL NMP and 0.25 mL DIPEA and 14 mg succimidyl-14-(N-malemidomethyl)cyclohexane-1-carboxylate (Pierce 22360) was added. The reaction was complete after 1 h. The product was precipitated with diethyl ether and purified by RP-HPLC, neutralized with DIPEA and freeze-dried to a colorless oil. Yield was 35 mg. MS calc. for C125H217N25O59 was 3014.239.

5: Flu-L120-Lys(NTA)-NH$_2$

Downloaded Boc-Lys(2-Cl-Z) resin, 500 mg, was Boc deprotected and subjected to two couplings with Boc-L60-OH. The Boc group was removed and carboxyfluorescein, 150 mg, activated with HBTU, 136 mg, and DIPEA, 70 µL, in 2 mL NMP was added to the resin. After 1 h coupling, the resin was washed and treated with 20% piperidine in DMF for 5 min. The resin was washed with TFA and the intermediate product (Flu-L120-Lys(NH2)-NH2) was cleaved from the resin and precipitated with diethyl ether. The product was resuspended in 500 µL NMP and 100 µL DIPEA and NTA-ditertbutyl ester, 9 mg, activated with succimidyl-N,N,N',N'-tetramethyluronium hexafluorophosphate, 10 mg, and 10 µL DIPEA in 50 µL NMP was added. After 10 min reaction, 50 µL piperidine was added, and after further 5 min, the product was precipitated with diethyl ether. The product was dissolved in 500 µL TFA, 50 µL TFMSA, 50 µL m-cresole, and after 10 min it was reprecipitated and purified by RP-HPLC. Yield was 26 mg. MS calc. for C113H176N20O was 2646.752, and the MS measured was 2646.

6: DNP-L120-Lys(Rho)-L120-Lys(NH$_2$)—NH

Downloaded Boc-Lys(2-Cl-Z) resin, 55 mg, was Boc deprotected and subjected to two couplings with Boc-L60-OH. Boc-Lys(Fmoc) was then coupled, followed by another two couplings with Boc-L60-OH. The Fmoc group was removed and tetramethylrhodamine carboxylic acid, 17 mg, activated with succimidyl-N,N,N',N'-tetramethyluronium hexafluorophosphate, 14 mg, and DIPEA 13 µL, in 400 µL NMP was added to the resin. After 30 min, the resin was washed and Boc deprotected, followed by treatment with 2,4-dinitrofluorobenzene, 19 mg, and DIPEA, 35 µL, 400 µL NMP. The product was cleaved from the resin, precipitated with diethyl ether and purified by RP-HPLC. Yield 6.5 mg. MS calc. for $C_{203}H_{336}N_{41}O_{90}$ was 4791.135, while MS found was 4778.3. (DNP loses oxygen in MS.)

7: Flu-L120-Lys(Flu)-L120-Lys(NTA)-NH$_2$

Downloaded Boc-Lys(2-Cl-Z) resin, 200 mg, was Boc deprotected and subjected to two couplings with Boc-L60-OH. Boc-Lys(Fmoc) was then coupled, followed by another two couplings with Boc-L60-OH. Both the Boc and the Fmoc group were removed and carboxyfluorescein, 75 mg, activated with HBTU, 68 mg, and DIPEA, 35 μL, in 1 mL NMP was added to the resin. After 1 h coupling, the resin was washed and treated with 20% piperidine in DMF for 5 min. The resin was washed with TFA and the intermediate product (Flu-L120-Lys(Flu)-L120-Lys(NH$_2$)—NH$_2$) was cleaved from the resin and precipitated with diethyl ether. The product was resuspended in 500 μL NMP and 100 μL DIPEA and NTA-di tertbutyl ester, 9 mg, activated with succimidyl-N,N, N',N'-tetramethyluronium hexafluorophosphate, 10 mg, and 10 μL DIPEA in 50 μL NMP was added. After 10 min reaction, 50 μL piperidine was added, and after further 5 min, the product was precipitated with diethyl ether. The product was dissolved in 500 μL TFA, 50 μL TFMSA, 50 μL m-cresole, and after 10 min it was reprecipitated and purified by RP-HPLC. Yield was 38 mg. MS calc. for $C_{220}H_{342}N_{38}O_{99}$ was 5103.347, while the MS measured was 5094.

8: Rho-L120-Lys(Flu)-L120-Lys(betaala)-NH$_2$

Downloaded Boc-Lys(Fmoc) resin, 100 mg, was Boc deprotected subjected to one coupling with Boc-Lys(Fmoc)-OH. The two Fmoc groups were removed and beta-alanine-N,N-diacetic acid benzyl ester coupled to the two side chain amino groups. The synthesis continued with 4×Boc-L30-OH, Boc-Lys(Fmoc)-OH and then 4×Boc-L30-OH. The Fmoc group was removed and carboxyfluorescein, 37 mg, activated with HBTU, 34 mg, and DIPEA, 17 μL, in 0.5 mL NMP was added to the resin for 30 min. The terminal Boc group was then removed and tetramethylrhodamine carboxylic acid, 17 mg, activated with succimidyl-N,N,N',N'-tetramethyluronium hexafluorophosphate, 14 mg, and DIPEA 13 μL, in 400 μL NMP was added to the resin. After 30 min coupling, the resin was treated with 20% piperidine in NMP. The resin was washed with DCM, then TFA, and the product was cleaved off the resin, precipitated with diethyl ether, and purified by RP-HPLC. Yield was 8 mg. MS calc. for $C_{238}H_{375}N_{43}O_{103}$ was 55486.838, while MS found was 5478.3.

9: Flu-L90-Lys(Flu)-L90-Lys(Flu)-L60-Lys(betaala)-Lys(betaala)-NH$_2$

Downloaded Boc-Lys(Fmoc) resin, 250 mg, was Boc deprotected and subjected to one coupling with Boc-Lys(Fmoc)-OH. The two Fmoc groups were removed and beta-alanine-N,N-diacetic acid benzyl ester coupled to the two side chain amino groups. The synthesis continued with 2× Boc-L30-OH, Boc-Lys(Fmoc)-OH, 3× Boc-L30-OH, Boc-Lys(Fmoc)-OH and finally with 3× Boc-L30-OH. The two Fmoc groups were removed, then the terminal Boc group. Carboxyfluorescein, 75 mg, activated with HBTU, 68 mg, and DIPEA, 35 μL, in 1 mL NMP, was added to the resin twice for 30 min, followed by 5 min treatment with 20% piperidine in NMP. The resin was washed with DCM, then TFA, and the product was cleaved off the resin, precipitated with diethyl ether and purified by RP-HPLC. Yield was 25 mg. MS calc. for $C_{261}H_{387}N_{43}O_{112}$ was 5919,183, while MS found was 5030.

10: Flu-L120-Lys(Flu)-L120-Lys(Flu)-L120-Lys(betaala)-Lys(betaala)-NH$_2$

Downloaded Boc-Lys(Fmoc) resin, 250 mg, was Boc deprotected subjected to one coupling with Boc-Lys(Fmoc)-OH. The two Fmoc groups were removed and beta-alanine-N,N-diacetic acid benzyl ester coupled to the two side chain amino groups. The synthesis continued with 4×Boc-L30-OH, Boc-Lys(Fmoc)-OH, 4×Boc-L30-OH, Boc-Lys(Fmoc)-OH and finally with 4×Boc-L30-OH. The two Fmoc groups were removed, then the terminal Boc group. Carboxyfluorescein, 75 mg, activated with HBTU, 68 mg, and DIPEA, 35 μL, in 1 mL NMP was added to the resin twice for 30 min, followed by 5 min treatment with 20% piperidine in NMP. The resin was washed with DCM, then TFA and the product was cleaved off the resin, precipitated with diethyl ether and purified by RP-HPLC. Yield was 34 mg. MS calc. for $C_{341}H_{531}N_{59}O_{152}$ was 7889.296, while MS found was 7885.

11: Flu-L120-Lys(Flu)-L120-Lys(Flu)-L120-Lys(Flu)-L120-Lys(betaala)-Lys(betaala)-NH, Downloaded Boc-Lys(Fmoc) resin, 250 mg, was Boc deprotected and subjected to one coupling with Boc-Lys(Fmoc)-OH. The two Fmoc groups were removed and beta-alanine-N,N-diacetic acid benzyl ester coupled to the two side chain amino groups. The synthesis continued with 4×Boc-L30-OH, Boc-Lys(Fmoc)-OH, 4×Boc-L30-OH, Boc-Lys(Fmoc)-OH, 4×Boc-L30-OH, Boc-Lys(Fmoc)-OH and finally with 4×Boc-L30-OH. The three Fmoc groups were removed, then the terminal Boc group. Carboxyfluorescein, 75 mg, activated with HBTU, 68 mg, and DIPEA, 354, in 1 mL NMP was added to the resin twice for 30 min, followed by 5 min treatment with 20% piperidine in NMP. The resin was washed with DCM, then TFA and the product was cleaved off the resin, precipitated with diethyl ether and purified by RP-HPLC. Yield was 25 mg. MS calc. for $C_{448}H_{697}N_{77}O_{199}$ was 10345.89, while MS found was 10336.

12: Flu-L120-Lys(Flu)-L120-Lys(Flu)-L120-Lys(Flu)-L120-Lys(Flu)-L120-Lys(betaala)-NH$_2$ Downloaded Boc-Lys(Fmoc) resin was Fmoc deprotected and beta-alanine-N,N-diacetic acid benzyl ester coupled to the side chain amino group. 50 mg of this resin was utilized for automated solid phase synthesis, coupling the sequence 4×Boc-L30-OH then Boc-Lys(Fmoc)-OH four times then finally 4×Boc-L30-OH. All four Fmoc groups and the terminal Boc group were removed, and the resin subjected to labeling with carboxyfluorescein for 3×1 h. The resin was treated with 20% piperidine in DMF, washed with NMP, DCM, TFA and the product cleaved off. Following precipitation with diethyl ether, it was purified by RP-HPLC. Yield was 7 mg. MS calc. for $C_{542}H_{942}N_{92}O_{240}$ was 12487.16, while MS found was 12463.

13: (betaala)-L60-Lys(Flu)-L240-TGTACCTTGA-NH$_2$

Downloaded Boc-PNA-A-resin, 50 mg, was used for automated synthesis on a 433A peptide synthesizer. First the appropriate 9 PNA monomers were coupled, then 8×Boc-L30-OH, then Boc-Lys(Fmoc)-OH and finally again 2×Boc-L30-OH. The resin was then manually Boc deprotected; coupled with beta-alanine-N,N-diacetic acid benzyl ester, then Fmoc deprotected and labeled with carboxyfluorescein on the lysine side chain. The product was cleaved off the resin, precipitated with diethyl ether and purified by RP-HPLC. Yield was 4.5 mg. MS calc. for $C_{342}H_{528}N_{98}O_{144}$ was 8316.547, while MS found was 8318.

Example 4

Linker Derivatives 14-19 and their Fluorescence Intensities

The following 6 PNAs with the same sequence but different linker and fluorescein constructs at one or both ends of the PNA were prepared by standard solid phase syntheses.

14: Ac-Lys(Flu)-L30-AACGGGATAACTGCACCT-L30-Lys(Flu)-L90-Lys(Flu)-NH$_2$. MW calc for $C_{376}H_{488}N_{134}O_{123}$ 8852.852. found 8855.

15: Ac-Lys(Flu)-L30-AACGGGATAACTGCACCT-L30-Lys(Flu)-L90-Lys(Flu)-L90-Lys(Flu)-NH$_2$. MW calc for $C_{463}H_{618}N_{148}O_{160}$ 10816.92. found 10819.

16: H-Lys(Flu)-L30-AACGGGATAACTGCACCT-L30-Lys(Flu)-L90-Lys(Flu)-L90-Lys(Flu)-NH$_2$. MW calc for C$_{461}$H$_{615}$N$_{148}$O$_{159}$ 10773.87. found 10777.

17: (Flu-L60)$_2$Lys-L30-AACGGGATAACTGCACCT-NH$_2$. MW calc for C$_{341}$H$_{452}$N$_{130}$O$_{114}$ 8196.159. found 8197.

18: Flu-L30-AACGGGATAACTGCACCT-NH$_2$. MW calc for C$_{234}$H$_{286}$N$_{112}$O$_{67}$ 5739.564. found 5741.9.

19: ((Flu-L60)$_2$-Lys-L60)$_2$-Lys-L30-AACGGGATAACT-GCACCT-NH$_2$. MW calc for C$_{555}$H$_{784}$N$_{166}$O$_{208}$ 13109.35. found 13113.6

The PNA sequence was directed at a repetitive DNA sequence in the centromere of the human chromosome 17, allowing the PNAs to be compared by FISH on metaphases. To erase specimen variation, each of the PNAs was mixed with a red fluorescent PNA directed at the same centromere region on chromosome 17, and the intensity of the red and green signals compared visually and quantified by the "Measure Intensity" function in the Leica QFISH program.

The intensity of the green signal derived from the different fluorescein labeled PNAs increased with the number of fluoresceins on the PNA, indicating little or no quenching of the fluorophores. The derivatives 15, 16 and 19, each comprising 4 fluorophores, gave more intense signals. The most intense of the three probes was derivative 16, indicating that its extra N-terminal free amino group relative to derivative 15 increased its affinity for DNA. Derivative 16 was also more intense than derivative 19, indicating that the linear design of 16 gave the probe easier access to the DNA than the branched dendrimer-like design of 19.

The fluorescence intensity of PNA conjugates according to this invention was also compared to that of conventionally labeled PNAs without linkers. Conventionally, the size of the PNA sequence limits the number of fluorophores that may be attached. For example, only two fluorophores can typically be attached to a 20-mer PNA as quenching becomes a problem with higher numbers of fluorophores. Further, guanine bases quench nearby fluorophores so that the intensity of a singly-labeled PNA probe typically falls to about 20-60% of the intensity of the fluorophore alone in solution. In contrast, the instant linker derivatives relieve those constraints. PNA-comprising linker derivatives may be labeled with four fluorescent labels, for example, giving 200% of the intensity of a free fluorescent probe in solution.

Example 5 Linker Derivatives 20-23

Protein Conjugates and their Fluorescence Intensities

Figure 4:
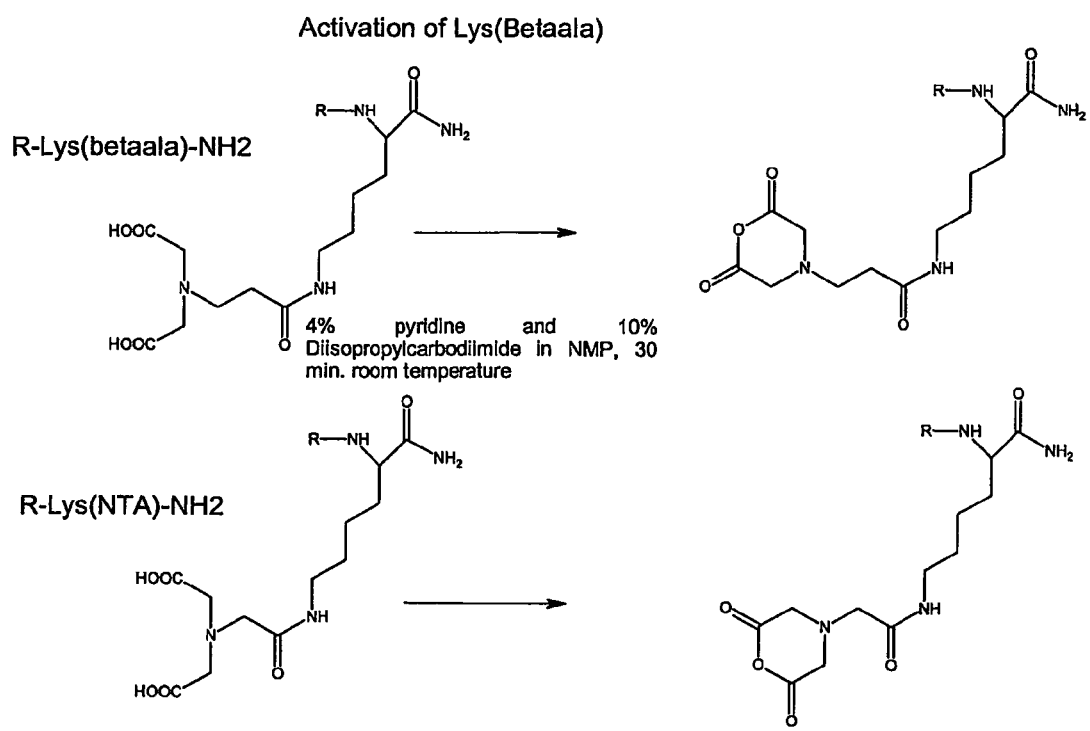
FIG. 4 depicts the activation of Lys(betaala)-$NH_2$ and Lys(NTA)-$NH_2$.

Linker derivatives 9, 10 and 11 were used for coupling to streptavidine. The betaalanine-N,N diacetic acid moieties on the linkers were converted to amino-reactive cyclic anhydrides by treatment with diisopropyl carbodiimide. We found that this method of activation was particularly suitable for conjugation in weakly basic aqueous environments, and was superior to NHS-ester activation and other cyclic anhydrides such as nitrillotriacetic acid (NTA). (See FIG. 4 for a depiction of the activation of Lys(betaala).) Not only did the cyclic anhydride of betaalanine-N,N-diacetic acid form quantitatively in 30 min, it also showed high selectivity for reacting with amino groups on proteins rather than being hydrolyzed by water.

Typical procedure: Linker derivative 10, 1 micromole, was dissolved in 86 µL NMP and 4 µL pyridine. Once dissolution was complete, 10 µL diisopropyl carbodiimide was added and the mixture allowed to stand for 30 min at room temperature. To confirm that the conversion to cyclic anhydride had taken place, 1 µL of the mixture was reacted with a large excess of primary amine (see, e.g., structure 3 of FIG. 1, 493 Da). MALDI-TOF mass spectroscopy confirmed that the desired activation had taken place. The activated linker was precipitated with diethyl ether, briefly dried in a stream of nitrogen, and redissolved in a solution of 2.6 mg streptavidine (50 nmol) in 100 µL 150 mM sodium hydrogen carbonate, pH 8.0. The reaction was complete after 10 min. The product was purified by size exclusion chromatography on a SUPERDEX® 200 column. Mass spectroscopy and UV measurements showed that 4 linker-comprising molecules with a total of 12 fluoresceins had been attached to the streptavidine.

Using the above procedure the following 4 conjugates were prepared:

20: Streptavidine with 4 linker derivatives, each comprising derivative 9 above. The conjugate comprised in total, 12 fluoresceins with L90 spacing between the fluorophores.

21: Streptavidine with 8 linker derivatives, each comprising derivative 9. In total, the conjugate comprised 24 fluoresceins with L90 spacing between the fluorophores.

22: Streptavidine with 4 linker derivatives, each comprising derivative 10 above. In total, the conjugate comprised 12 fluoresceins with L120 spacing between the fluorophores.

23: Streptavidine with 4 linker derivatives, each comprising derivative 11 above. The conjugate comprised in total, 16 fluoresceins with L120 spacing between the fluorophores.

The fluorescence of the three linker derivatives 9, 10 and 11, the 4 streptavidine conjugates 20, 21, 22; and 23, and a conventionally FITC-labeled streptavidine conjugate with two attached fluoresceins (F422 of Dako with 2 FITC/streptavidine) was determined. All compounds were prepared as 100 nM total fluorescein solutions in 150 mM carbonate pH 8, using 100 nM free carboxy fluorescein as a reference for normalization of the relative intensities. The solutions were excited at 488 nm, and the fluorescence intensity read at 520 nm. The results are presented in the following table:

| Compound | intensity at 520 nm (arbitrary units) | relative intensity for each fluorescein | total intensity for compound = relative intensity × number of fluoresceins |
|---|---|---|---|
| carboxy fluorescein | 884 | 1.000 (reference) | 1.000 (reference) |
| 9 | 517 | 0.58 | 1.75 |
| 10 | 592 | 0.67 | 2.01 |
| 11 | 535 | 0.61 | 2.42 |
| 20 | 233 | 0.26 | 3.16 |
| 21 | 161 | 0.18 | 4.38 |
| 22 | 260 | 0.29 | 3.53 |
| 23 | 240 | 0.27 | 4.34 |
| F422 | 411 | 0.46 | 0.93 |

As can be seen, the linker derivatives of the present invention are up to several fold more intense than the F422 conventionally labeled streptavidine. Further, as expected, the longer the linkers and hence the more spacing there was between the individual fluorophores, the less quenching was observed. Indeed, very little quenching was observed for the free linker derivatives 9, 10 and 11, strongly indicating that the linkers were fully extended in water.

As more linkers were built into the same conjugate, quenching was evidently increased as linkers were immobilized on the streptavidine. (Compare 20 to 21 for example.) However the sheer number of fluoresceins that could be conjugated via the linker derivatives easily compensated for this, allowing preparation of conjugates with 4-5 times the fluorescence intensity normally used by conventional, prior art methods.

Example 6

Linker Derivatives Comprising PNAs with Non-Natural Bases

Part A: Exemplary Embodiments of PNA Sequences
All made by PNA standard procedures (see Example 2)

| SEQUENCE DESIGNATION | PNA SEQUENCES[1] | N-TERMINAL | C-TERMINAL | MOLECULAR WEIGHT |
|---|---|---|---|---|
| SEQ. AA | TCD-DG$_s$G$_s$-TAC-A | FLU-L$_{30}$- | -LYS(CYS) | 8805 |
| SEQ. AB | U$_s$GU$_s$-DPP-TTG-D | FLU-L$_{30}$- | -LYS(CYS) | 8727 |
| SEQ. AC | CU$_s$G$_s$-G$_s$DD-TU$_s$D-G$_s$DC | FLU-L$_{30}$- | -LYS(CYS) | 9413 |
| SEQ. AD | GTP-TAA-TTP-PAG | FLU-L$_{30}$- | -LYS(CYS) | 9203 |
| SEQ. AE | DG$_s$T-CG$_s$D-DG$_s$G-U$_s$CU$_s$ | FLU-L$_{30}$- | -LYS(CYS) | 9413 |
| SEQ. AF | AGA-CPT-TPG-APT | FLU-L$_{30}$- | -LYS(CYS) | 9187 |
| SEQ. AG | TCD-DI I-TAC-A | FLU-L$_{30}$- | -LYS(CYS) | 8742 |

[1]Flu is fluorescein; T is thiamine; C is cytosine; D is diaminopurine; G$_s$ is thioguanine; A is Adenine; U$_s$ is 2/4-thiouracil; G is guanine; P is pyrimidinone; I is Inosine.

Part B—Three PNAs with the L$_{30}$ Linker with Different Amino Acids at the C-Terminal BA: Flu-L$_{30}$-DGT-DTC-GTD-CCG-Lys(Acetyl)

BB: Flu-L$_{30}$-DGT-DTC-GTD-CCG-Lys(Cys)

BC: Flu-L$_{30}$-DGT-DTC-GTD-CCG-Lys(Lys)$_3$

Part C—Synthesis of Flu-L$_{90}$-Lys(Flu)-L$_{30}$-Lys Cys)

Using the resin downloading procedure provided in Example 2, an MBHA-resin was loaded with Boc-Lys(Dde)-OH. Using a peptide synthesizer, amino acids were coupled according to PNA solid phase procedure provided in Example 2 yielding Boc-L$_{90}$-Lys(Fmoc)-L$_{30}$-Lys(Dde). The Boc and Fmoc protections groups were removed and the amino groups marked with flourescein using the procedure in Example 2. Then, the Dde protection group was removed and 0.4 M cysteine was added according to the procedure in Example 2. The PNA was cleaved the resin, precipitated with ether and purified on HPLC according to Example 2. The product was found to have a molecular weight of 3062 using MALDI-TOF mass spectrometry; the calculated molecular weight is 3061.

Example 7

Synthesis of Dextran Conjugates

Conjugate Made from Sequence AA from Example 6, DexVS70, and Flu(10)

Dextran (with a molecular weight of 70 kDa) was activated with divinylsulfone to a degree of 92 reactive groups/dextran polymer; this product is designated DexVS70.

| 280 μL DexVS70 | 20 nmol |
| 66 μL Flu$_2$Cys | 160 nmol (prepared from |

25 μL 0.8 M NaHCO$_3$ pH=9.5
29 μL H$_2$O

The above four compounds were mixed. The mixture was placed in a water bath at 30° C. for 16 hours. The mixture was added to 50 nmol of freeze dried PNA (sequence AA). The mixture was placed in a water bath at 30° C. for 30 minutes. The conjugating reaction was quenched with 50 μL of 500 mM cysteine for 30 minutes at 30° C. Purification of the product was performed using FPLC: column SUPERDEX®—200, buffer 10 mM Hepes 100 mM NaCl, methode 7 bank 2, Loop 1 mL. Two fractions were collected: one with the product and one with the residue. The relative absorbance Flu$_2$ ($\epsilon_{500\ nm}$=146000 M$^{-1}$, $\epsilon_{260\ nm}$=43350 M$^{-1}$) and PNA ($\epsilon_{500\ nm}$=73000 M$^{-1}$, $\epsilon_{260\ nm}$=104000 M$^{-1}$) was used to calculate the average conjugation ratio of Flu$_2$, PNA, and DexVS70. The conjugation ratio of Flu$_2$ to DexVS70 was 9.4. The conjugation ratio of PNA (sequence AA) to DexVS70 was 1.2.

HRP-DexVS70-Seq. AA

Using the procedure for the standard synthesis of HRP-DexVS70-PNA conjugate, the conjugate HRP-DexVS70-Seq. AA was made. The ratio of HRP to DexVS70 is 12.2; the ratio of Seq. AA to Dex70 is 1.2.

GaM-DexVS70-Seq. AB

The synthesis of GaM-DexVS70-Seq. AB was performed using the procedure in Example 17 with the following changes as indicated.

Dextran (molecular weight 70 kDa) is activated with divinylsulfone to a degree of 92 reactive groups/dextran polymer.

| 105.0 μL DexVS70 | 7.5 nmol |
| 57.0 μL Goat anti mouse Imuno globuline (GAM-Ig) | 15 nmol |
| 8.9 μL 4 M NaCl | |
| 10.6 μL 0.8 M NaHCO$_3$ (pH = 9.5) | |
| 144.5 μL H$_2$O | |

The above five components were mixed and placed in a water bath at 30° C. for 40 minutes. Two hundred and ninety μL were taken out of the mixture and added to 100 nmol of Seq. AB, which was previously dissolved in 80 μL of H$_2$O. Then, 20 μL of 0.8 M NaHCO$_3$ (pH 9.5) was added and the mixture placed in a water bath at 30° C. for 1 hour. Quenching was performed by adding 39 μL of 500 mM Cysteine and letting the resultant mixture set for 30 minutes at 30° C.

Purification of the product on FPLC: column SUPERDEX®—200, buffer 10 mM Hepes 100 mM NaCl, method 7 bank 2, Loop 1 mL. Two fractions were collected: one with the product and one with the residue. Relative absorbance PNA(Flu) ($\epsilon_{500\ nm}$=73000 M$^{-1}$) and GAM ($\epsilon_{278\ nm}$=213000 M$^{-1}$) (correction factor for PNA at 278 nm is due to the specific PNA and is calculated: 278/500 nm) was used to calculate the average conjugation ratio of PNA, GAM and DexVS70. The ratio of PNA to DexVS70 was 5.3 and the ratio of GaM to DexVS70 was 0.8.

Exemplary Embodiments of PNA1-DexVS-PNA2 Conjugates

| Conjugate designation | ratio | PNA1 | PNA1 nmol | PNA1 to DexVS | PNA2 | PNA2 nmol | PNA2 to DexVS | DexVS |
|---|---|---|---|---|---|---|---|---|
| Conj. CA | 1:9 | Seq. AA | 12.5 | 1.02 | Seq. AD | 100 | 8.2 | DexVS70 |
| Conj. CB | 1:6 | Seq. AC | 40 | 1.5 | Seq. AB | 200 | 7.4 | DexVS70 |
| Conj. CC | 1:16 | Seq. AC | 13.3 | 0.84 | Seq. AB | 200 | 12.7 | DexVS150 |
| Conj. CD | 1:6 | Seq. AC | 40 | 2.3 | Seq. AB | 200 | 11.5 | DexVS150 |

All conjugates were made by standard conjugation procedures described for the synthesis of PNA1-DexVS70-PNA2.

Anti-Human-BCL2-DexVS70-PNA

Dextran (molecular weight 70 kDa) was activated with divinylsulfone to a degree of 92 reactive groups/dextran polymer, and is designated DexVS70. The antibody Anti-Human-BCL2 is designated AHB.

| | |
|---|---|
| 105 μL DexVS70 | 7.5 nmol |
| 800 μL AHB conc. (2.9 g/L) | 15.1 nmol |
| 25 μL 4 M NaCl | |
| 32 μL 0.8 M NaHCO$_3$ (pH = 9.5) | |

The above four compounds were mixed and placed in a water bath at 30° C. for 65 minutes. From this mixture, 875 μL was taken out and added to the indicated number of nmol of PNA in the table below; before the addition the PNA had been dissolved in the μL of H$_2$O indicated in the table below. Then the number of μLs of 0.8 M NaHCO$_3$ (pH 9.5) was added according to the table below. The resulting mixture was placed in a water bath at 30° C. for 70 minutes. Quenching was performed by adding 6 mg of solid cysteine (0.05 M) to the mixture and letting it stand for 30 minutes at 30° C.

Purification of the product on FPLC: column SUPERDEX®—200, buffer 10 mM Hepes 100 mM NaCl, method 7 bank 2, Loop 1 mL. Two fractions were collected: one with the product and one with the residue. Relative absorbance PNA(Flu) ($\epsilon_{500\ nm}$=73000 M$^{-1}$) and AHB ($\epsilon_{278\ nm}$=213000 M$^{-1}$) (correction factor for PNA at 278 nm is due to the specific PNA and is calculated: 278/500 nm) was used to calculate the average conjugation ratio of PNA, AHB and DexVS70.

Conjugates with Different Ratios PNA

| Conjugate designation | nmol of PNA added | μL of H$_2$O added | μL of 0.8 M NaHCO$_3$(pH 9.5) added | PNA to DexVS70 | AHB to DexVS70 |
|---|---|---|---|---|---|
| Conj. DA | 100 | 75 | 25 | 9.5 | 1.6 |
| Conj. DB | 33 | 30 | 10 | 2.9 | 1.2 |
| Conj. DC | 67 | 60 | 20 | 5.6 | 1.1 |

Example 7

Solid Phase Synthesis and Purification of Lys(Flu)-L$_{30}$-chr 17:14-L$_{30}$-Lys(Flu)-L$_{90}$-Lys(Flu)-L$_{90}$-Lys(Flu)

All Standard procedures are described in Example 2.

1. An MBHA-resin was loaded with Boc-L$_{30}$-Lys(Fmoc)-L$_{90}$-Lys(Fmoc)-L$_{90}$-Lys(Fmoc) using a standard loading procedure to a loading of 0.084 mmol/g.

2. To this resin, Boc-Lys(Fmoc)-L$_{30}$-AAC-GGG-ATA-ACT-GCA-CCT- was coupled using the peptide synthesizer machine following standard PNA solid phase chemistry. Fmoc protection groups were removed and the amino groups were labeled with fluorescein. After cleaving and precipitation the PNA was dissolved in TFA. The precipitate was washed with ether. The precipitate was dissolved in 200 μL NMP To this solution 6 mg Fmoc-Osu was added and dissolved. Next, DIPEA (9 μL) was added and the reaction was followed using MALDI-TOF mass spectrometry. After 30 minutes the reaction was finished and the PNA was precipitated and washed with ether.

HPLC after dissolving the PNA in 30% CH$_3$CN and 10% TFA/H$_2$O gave three pure fractions. The fractions were pooled and lyophilized. The lyophilized PNA was then dissolved in 192 μL NMP. Piperidine (4 μL) and 4 μL DBU was added to this solution which set for 30 minutes. Analysis by MALDI-TOF mass spectrometry gave a molecular weight of 10777.

The precipitate was washed with ether and was then dissolved in 100 μL TFA. The precipitate was washed with ether and then dried using N$_2$ gas.

Example 8

Standard Synthesis of HRP-DexVS70-PNA Conjugate

Dextran (molecular weight 70 kDa) is activated with divinylsulfone to a degree of 92 reactive groups/dextran polymer.

| | |
|---|---|
| 192 μL DexVS70 | 13.7 nmol |
| 255 μL horse radish peroxidase (HRP) | 602 nmol |
| 15 μL 4 M NaCl | |
| 19 μL 0.8 M NaHCO$_3$ pH = 9.5 | |
| 119 μL H$_2$O | |

The above five components are mixed together placed in a water bath at 30° C. for 16 hours. Five hundred microliters of this mixture are added to 50 nmol PNA, which is previously dissolved in 40 μL H$_2$O. Then, 10 μL of 0.8 M NaHCO$_3$ (pH 9.5) is added. The mixture is then placed in a water bath at 30° C. for 2 hours. Quenching is performed by adding 55 μL of 110 mM Cysteine and letting the resultant mixture set for 30 minutes at 30° C.

Purification of the product is performed by FPLC: column SUPERDEX®—200, buffer 10 mM Hepes 100 mM NaCl, methode 7 bank 2, Loop 1 mL.

Two fractions are collected: one with the product and one with the residue. Relative absorbance HRP ($\epsilon_{404\ nm}$=83000 M$^{-1}$, $\epsilon_{500\ nm}$=9630 M$^{-1}$) and PNA(Flu) ($\epsilon_{500\ nm}$=73000 M$^{-1}$) is used to calculate the average conjugation ratio of HRP, PNA and DexVS70.

Example 9

Additional Methods of Synthesis of AP-DexVS70-PNA Conjugate

Alkaline Phosphatase ("AP") (from Calf Intestine, EIA grade) was dialyzed overnight against 2 mM HEPES, pH 7.2; 0.1M NaCl; 0.02 mM $ZnCl_2$. Dextran (molecular weight 70 kDa) was activated with divinylsulfone to a degree of 92 reactive groups per dextran polymer (DexVS70).

The three components below were mixed together and placed in a water bath at 40° C. for 30 minutes.

| | |
|---|---|
| 192.0 µL DexVS70 | 13.7 nmol |
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| | |
|---|---|
| 160.0 µL AP | 43.4 nmol |
| 7.7 µL 1M $NaHCO_3$ | |
| 30.6 µL 20 mM Hepes, pH 7.2; 1M NaCl; 50 mM $MgCl_2$; 1 mM $ZnCl_2$ | |

The mixture was placed in a water bath at 40° C. for 3 hours. Quenching was performed by adding 30.6 µL of 0.1 M ethanolamine and letting the mixture stand for 30 minutes in water bath at 40° C. The product was purified on FPLC with: Column Superdex-200, buffer: 2 mM HEPES, pH 7.2; 0.1M NaCl; 5 mM $MgCl_2$; 0.1 mM $ZnCl_2$. Two fractions were collected, one with the product and one with the residue.

In comparison to the experiment described above, another conjugate was made with extended conjugation time. The three components below were mixed together and placed in a water bath at 40° C. for 30 minutes.

| | |
|---|---|
| 192.0 µL DexVS70 | 13.7 nmol |
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| | |
|---|---|
| 160.0 µL AP | 43.4 nmol |
| 7.7 µL 1M $NaHCO_3$ | |
| 30.6 µL 20 mM Hepes, pH 7.2; 1M NaCl; 50 mM $MgCl_2$; 1 mM $ZnCl_2$ | |

The mixture was placed in a water bath at 40° C. for 5 hours. Quenching was performed by adding 30.6 µL 0.1M Ethanolamine and letting the mixture stand for 30 minutes in water bath at 40° C. Purification of the product on FPLC: Column Superdex-200, buffer: 2 mM Hepes, pH 7.2; 0.1M NaCl; 5 mM $MgCl_2$; 0.1 mM $ZnCl_2$. Two fractions were collected: One with the product and one with the residue.

Relative absorbance PNA(Flu) ($\epsilon_{500\ nm}$=73000$M^{-1}$) and AP ($\epsilon_{278\ nm}$=140000$M^{-1}$. Corrected for absorbance from PNA at 278 nm, this correction factor is due to the specific PNA and it is calculated: 278/500 nm) was used to calculate the average conjugation ratio of PNA, AP and DexVS70.

AP-DexVS70-PNA, 3 hrs:
PNA/DexVS70: 1.8
AP/DexVS70: 1.8
AP-DexVS70-PNA, 5 hrs:
PNA/DexVS70: 2.0
AP/DexVS70: 2.4

Due to these results, it is recommended to follow a procedure in which the conjugation time (AP+DexVS70-PNA) is 5 hours.

Example 10

Standard Synthesis of GAM-DexVS70-PNA Conjugate

Dextran (molecular weight 70 kDa) is activated with divinylsulfone to a degree of 92 reactive groups/dextran polymer (DexVS70).

| | |
|---|---|
| 105.0 µL DexVS70 | 7.5 nmol |
| 57.0 µL Goat anti mouse Imuno globuline (GAM) | 15 nmol |
| 8.9 µL 4 M NaCl | |
| 10.6 µL 0.8 M $NaHCO_3$ (pH = 9.5) | |
| 144.5 µL $H_2O$ | |

The above five components are mixed and placed in a water bath at 30° C. for 40 minutes. Two hundred and ninety µL is taken out of the mixture and added to 50 nmol of PNA, which is previously dissolved in 40 µL of $H_2O$. Then, 10 µL of 0.8 M $NaHCO_3$ (pH 9.5) is added and the mixture placed in a water bath at 30° C. for 1 hour. Quenching is performed by adding 34 µL of 500 mM Cysteine and letting the resultant mixture set for 30 minutes at 30° C.

Purification of the product on FPLC: column SUPERDEX®—200, buffer 10 mM Hepes 100 mM NaCl, method 7 bank 2, Loop 1 mL. Two fractions are collected: one with the product and one with the residue. Relative absorbance PNA (Flu) ($\epsilon_{500\ nm}$=73000 $M^{-1}$) and GAM ($\epsilon_{278\ nm}$=213000 $M^{-1}$. Correction factor for PNA at 278 nm is due to the specific PNA and is calculated: 278/500 nm) was used to calculate the average conjugation ratio of PNA, GAM and DexVS70.

Example 11

Standard Synthesis of PNA1-DexVS70-PNA2

Dextran (molecular weight 70 kDa) is activated with divinylsulfone to a degree of 92 reactive groups/dextran polymer. PNA1 (100 nmol) is dissolved in 140 µL of DexVS70 (10 nmol). To this mixture 12.5 µL of PNA2 (12.5 nmol) dissolved in $H_2O$ is added, and then 30 µL of $NaHCO_3$ (pH 9.5) is added and the solution mixed. The resultant mixture is placed in a water bath at 30° C. for 35 minutes. Quenching was performed by adding 18.3 µL of 500 mM Cysteine in Hepes and letting this mixture set for 30 minutes at 30° C.

Purification of the product on FPLC: column SUPERDEX®—200, buffer 10 mM Hepes 100 mM NaCl, methode 7 bank 2, Loop 1 mL. Two fractions are collected: one with the product and one with the residue. Relative absorbance PNA(Flu) ($\epsilon_{500\ nm}$=73000 $M^{-1}$) and the proportion between the two PNA's is used to calculate the average conjugation ratio of PNA, PNA and DexVS70.

Example 12

Synthesis of the Boc-PNA-I(O-Bz)-Monomer

6-Benzyloxypurine

Sodiumhydride (60% Dispersion in mineral oil; 3.23 g; 80 mmol) was slowly added to Benzylalkohol (30 ml; 34.7 mmol). After the addition of more benzylalkohol (10 ml) and 6-chloropurine (5.36 g). The reaction mixture was heated to 100° C. for 4 hours. When the reaction mixture has reached room temperature, water (1 ml) was slowly added. 6-Benzyloxypurine was precipitated by the addition of acetic acid (4.6 ml) and diethylether (550 ml). The precipitate was separated by filtration (11.72 g). Recrystallization from ether gave (4.78 g; 65.4%). Melting point 175-177° C. (litt. 170-172° C.) [Ramazaeva N., 1989 #473] 1H-NMR (DMSO-d6): 8.53 (1H, s); 8.39 (1H, s); 7.54-7.35 (5H, m); 5.62 (2H, s).

Methyl(6-(Benzyloxy)purin-9-yl)acetate

6-Benzyloxypurine (4.18 g; 18.5 mmol) was added to a suspension of potasiumcarbonate (3.1 g; 22.4 mmol) in DMF (100 ml). After 15 min. bromoacetic acid methyl ester (1.93 ml; 20.4 mmol) was added. The reaction was monitored by TLC in butanol:acetic acid:water 4:1:1. Upon completion, the reaction mixture was portioned between water (600 ml) and ethylacetate (600 ml). The organic phase was dried over magnesium sulphate and evaporated to a volume of ~10 ml and precipitated with pet. ether. The two products were separated by column chromatography using ethylacetate as the solvent. The products was precipitated in pet. ether. Yield: 2.36 g (43%). Melting point: 111.5-115° C. UV λmax=250 nm (9-alkylated); λmax=260 nm (7-alkylated). 1H-NMR (DMSO-d6): 8.60 (1H, s); 8.43 (1H, s); 7.6-7.35 (5H, m); 5.69 (2H, s); 5.26 (2H, s); 3.75 (3H, s).

(6-(Benzyloxy)purin-9-yl)acetic acid

Methyl(6-(Benzyloxy)purin-9-yl)acetate (2.10 g; 7.0 mmol) was dissolved in methanol (70 ml) and 0.1 M NaOH (85 ml) is added. After 15 min. the pH of the reaction mixture was lowered by addition of 0.1 M HCl (~80 ml) to pH 3. The precipitate was separated from the mixture by filtration and washed with water and ether. Yield: 1.80 g (90.2%). 1H-NMR (DMSO-d6): 8.55 (1H, s); 8.37 (1H, s); 7.55-7.30 (5H, m); 5.64 (2H, s); 5.09 (2H, s).

N-((6-(Benzyloxy)purin-9-yl)acetyl)-N-(2-Boc-aminoethyl)glycine

Ethyl N-(2-Boc-aminoethyl)glycinate (0.285 g; 1.15 mmol), (6-(Benzyloxy)purin-9-yl)acetic acid (0.284 g; 1.0 mmol) and 3-hydroxy-1,2,3 benzotriazin-4(3H)-one (0.180; 1.1 mmol) was dissolved in dichlormet-hane/dimethylforamide 1:1 (10 ml). After addition of dicycloehexylcarbodiimide (0.248 g; 1.2 mmol) the reaction was left over night. The precipitate was removed by filtration. The organic phase was extracted twice with saturated sodiumbicarbonate, dried with magnesiumsulphate and evaporated to a oil. Column purification on silica using dichlormethane with 0-5% methanol as elutant yields the monomer ester which was dissolved in methanol (10 ml). 0.1 M Sodiumhydroxide (12 ml) was added. After 30 min the reaction was filtered and pH adjusted with saturated KHSO4/water (1:3) to 2.7. The water phase was extracted twice with ethylacetate (2×100 ml). The combined organic phases were dried over magnesium sulfate and evaporated to a volumen of 10 ml. Precipitation with pet. ether yielded the monomer (0.15 g; 31%). 1H-NMR (DMSO-d6): 8.51 (1H, s); 8.23 (1H, s); 7.6-7.3 (5H, m); 5.64 (2H, s); 5.31 (ma.) +5.13 (mi.) (2H, s); 4.23 (mi.) +3.98 (ma.) (2H, s); 3.55-3.00 (4H, m); 1.36 (9H, s).

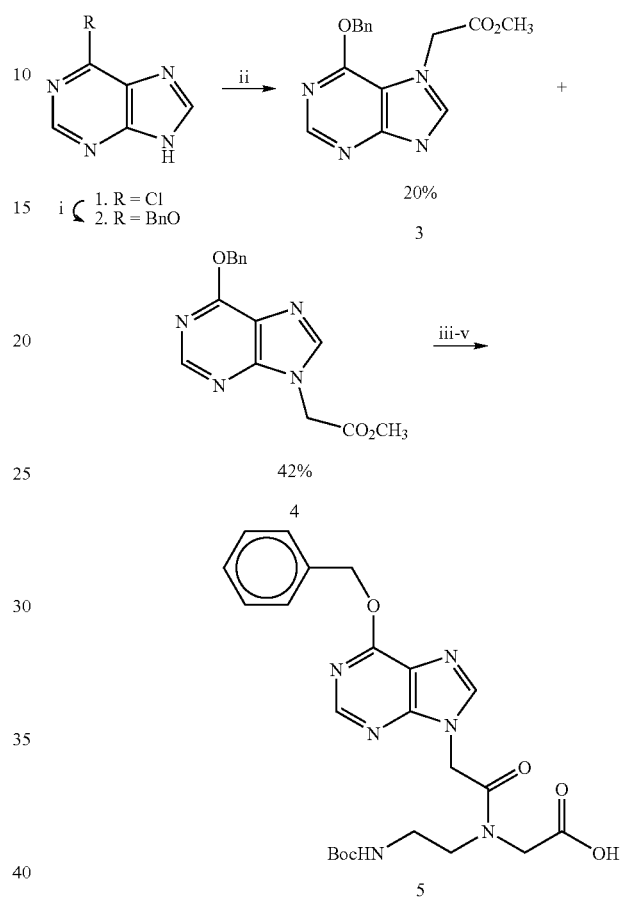

The synthesis of the hypoxanthine PNA monomer. (i) BnOH, NaH (ii) K2CO3, BrCH2CO2CH3 (iii) OH— (iv) DCC, Dhbt-OH, Boc-aeg-OEt (v) OH—

The Boc-PNA-Diaminopurine-(N6-Z)-monomer was prepared according to Gerald Haaima, Henrik F. Hansen, Leif Christensen, Otto Dahl and Peter E. Nielsen; Nucleic Acids Research, 1997, Vol 25, Issue 22 4639-4643

The Boc-PNA-2-Thiouracil-(S-4-MeOBz)-monomer was prepared according to Jesper Lohse, Otto Dahl and Peter E. Nielsen; Proceedings of the National Academy of Science of the United States of America, 1999, Vol 96, Issue 21, 11804-11808.

The Boc-PNA-Adenine-(Z)-monomer was from PE Biosystems catalog GEN063011.

The Boc-PNA-Cytosine-(Z)-monomer was from PE Biosystems cat. GEN063013.

The Boc-PNA-Guanine-(Z)-monomer was from PE Biosystems cat. GEN063012.

The Boc-PNA-Thymine-monomer was from PE Biosystems cat. GEN063010.

IsoAdenine (2-aminopurine) may be prepared as a PNA-monomer by 9-N alkylation with methylbromoacetate, protection of the amino group with benzylchloroformate, hydrolysis of the methyl ester, carbodiimide mediate coupling to methyl-(2-Boc-aminoethyl)-glycinate, and finally hydrolysis of the methyl ester.

4-thiouracil may be prepared as a PNA-monomer by S-protection with 4-methoxy-benzylchloride, 1-N alkylation with methylbromoacetate, hydrolysis of the methyl ester, carbodiimide mediate coupling to methyl-(2-Boc-aminoethyl)-glycinate, and finally hydrolysis of the methyl ester.

Thiocytosine may be prepared as a PNA monomer by treating the Boc-PNA-cytosine(Z)-monomer methyl ester with Lawessons reagent, followed by hydrolysis of the methyl ester.

A number of halogenated bases are commercially available, and may be converted to PNA monomers analogously to the non-halogenated bases. These include the guanine analog 8-bromo-guanine, the adenine analogs 8-bromo-adenine and 2-fluoro-adenine, the isoadenine analog 2-amino-6-chloro-purine, the 4-thiouracil analog 5-fluoro-4-thio-uracil, and the 2-thiouracil analog 5-chloro-2-thiouracil.

Boc-PNA-Uracil monomers were first described in "Uracil og 5-bromouracil I PNA," a bachelor project by Kristine Kilså Jensen, Københavns Universitet 1992.

Example 13

PNA with Positive and Negative Loadings

In order to make better conjugations at one time giving PNA, a loading was attempted. Both PNA's were made by PNA standard procedures (See Example 2).
1. Flu-$L_{30}$-Glu-TCA-AGG-TAC-A-Glu-$L_{300}$-Lys(Cys)
Glu=glutamate has negative loadings and for the easiness the PNA is designated −A4−
2. Flu-$L_{30}$-Lys(Me)$_2$-TGT-ACC-TTG-A-Lys(Me)$_2$-$L_{330}$-Lys(cys)
Lys(Me)$_2$=Boc-Lys(Me)$_2$-OH has positive loadings and the PNA is designated +T+

| name | number | HRP | GaM | equiv. | HRP/Dex | GaM/Dex | PNA/Dex |
|---|---|---|---|---|---|---|---|
| −A4− | D13041 | D13050 | | 9 | 12.3 | | 0.13 |
| −A4− | D13041 | | D13060 | 7 | | 0.94 | 0.66 |
| +T4+ | D13042 | D13058 | | 9 | 13.5 | | 0.19 |
| +T4+ | D13042 | | D13056 | 7 | | 1.42 | 0.45 |

Example 14

Further Linker Derivatives 100 mg MBHA resin was downloaded to a loading of 0.1 mmol/g with Boc-Lys(Fmoc) and subjected to repeated cycles of coupling with Boc-L30-free acid. Each coupling was performed with 48 mg Boc-L30-free acid activated with 23 mg HATU and 14 mg DIPEA in 0.9 mL NMP. After 20 cycles a small sample was cleaved of the resin, precipitated with diethyl ether, and subjected to mass spectroscopy.

This confirmed the expected structure:
H-L600-Lys(Fmoc)-NH$_2$ calc. for $C_{421}H_{744}N_{83}O_{203}$ 10217.00. found 10214.63

The resin was subjected to further 8 cycles of coupling with Boc-L30-free acid. Again a small sample was cleaved off the resin for analysis. Again the expected structure was confirmed:
H-L840-Lys(Fmoc)-NH$_2$ calc. for $C_{581}H_{1032}N_{115}O_{283}$ 14157.23. found 14153.4

The resin was subjected to further 5 cycles of coupling with Boc-L30-free acid. Again a small sample was cleaved off the resin for analysis. Again the expected structure was confirmed:
H-L990-Lys(Fmoc)-NH$_2$ calc. for $C_{681}H_{1212}N_{135}O_{333}$ 16619.87. found 16618.88

50 mg of the resin was then Boc deprotected and labeled with carboxy fluorescein. The Fmoc group on the lysine was removed, and the product was cleaved off the resin and precipitated with diethyl ether. It was resuspended in TFA and again precipitated. The product was dissolved in water and the absorbance at 500 nm used to quantify the yield of full length fluorescein labeled product. The yield was 1470 nm, 24 mg, corresponding to 29% over all yield for the 33 couplings with L30, corresponding to an average coupling yield of 96.3%. The structure was confirmed by mass spectroscopy, and there was no evidence of any major impurities.
Flu-L990-Lys(NH$_2$)—NH$_2$ calc. for $C_{687}H_{1213}N_{135}O_{337}$ 16756.94. found 16752.49.

Example 15

Alternative Linker Synthesis Method

Figure 8:
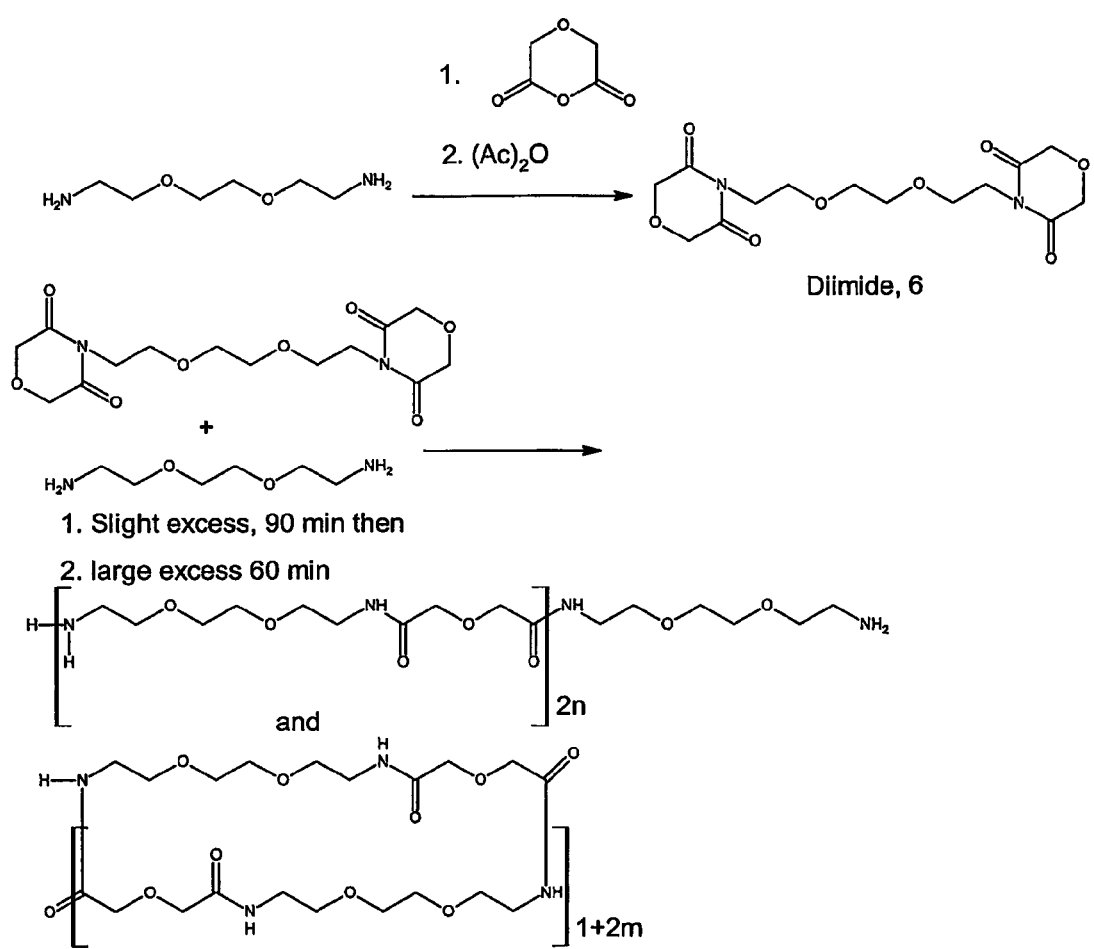
FIG. 8 depicts another exemplary method of preparing linkers according to the invention.

Synthesis of Diimide
See FIG. 8, structure 6. 2,2'(Ethylenedioxy)bis(ethylamine), 2.96 g, 20 mmol, in pyridine, 10 mL, was reacted with 5.8 g, 50 mmol, diglycolic anhydride for 5 min at 80° C. Acetic anhydride, 5 mL was added and the mixture stirred for further 1 h at 100° C. The solvents were evaporated off, and the residue stirred with 20 mL water for 30 min. The product was extracted into 100 mL DCM, and washed with 100 mL 1 M sodium citrate pH 4.5, 100 mL 1 M sodium hydrogen carbonate and then finally water. The DCM was evaporated of to give 5.3 g, 77%, colorless oil that solidified to a white mass over time.

Polymerization of Diimide and excess 2,2'(Ethylenedioxy)bis(ethylamine)

344 mg diimide, 1 mmol, and 160 mg 2,2'(Ethylenedioxy)bis(ethylamine) 1.08 mmol were dissolved in 0.5 mL NMP. The mixture was heated to 95° C. for 90 min. Further 148 mg, 1 mmol
2,2'(Ethylenedioxy)bis(ethylamine) was added the mixture heated for further 60 min. The crude reaction mixture was analyzed by MALDI-TOF mass spectroscopy. This showed that a mixture of cyclic and linear products had formed. There was evidence of cyclo-L30 (m=0) and cyclo L60 (m=1), but no higher cyclic oligomers. The linear oligomers comprised from n=1 to n=9. See FIG. 8 and structures below:
Cyclic:
m=0; calc for $C_{20}H_{36}N_4O_{10}$ 492.5282. found 492.23
m=1; calc for $C_{40}H_{72}N_8O_{20}$ 985.0564. found 985.039
Linear:
n=1; calc for $C_{26}H_{52}N_6O_{12}$ 640.7334. found 640.23
n=2; calc for $C_{46}H_{88}N_{10}O_{22}$ 1133.26. found 1132.02
n=3; calc for $C_{66}H_{124}N_{14}O_{32}$ 1625.29. found 1624.80
n=4; calc for $C_{86}H_{160}N_{18}O_{42}$ 2118.3. found 2117.6
n=5; calc for $C_{106}H_{196}N_{22}O_{52}$ 2610.84. found 2609.53
n=6; calc for $C_{126}H_{232}N_{26}O_{62}$ 3103.37. found 3101.48
n=7; calc for $C_{146}H_{268}N_{30}O_{72}$ 3595.90. found 3593.54
n=8; calc for $C_{166}H_{304}N_{34}O_{82}$ 4088.42. found 4086.74
n=9; calc for $C_{186}H_{340}N_{38}O_{92}$ 4580.95. found 4580.02.

Example 16

Method of Synthesizing Mono and 2,4-diamino-pyrimidine-5-yl PNA Monomers 2,4-diamino-pyrimidine-5-yl may be introduced into DNA-oligomers by methods known in the art (e.g. S. A. Benner, et al., *Nucleic Acid Research* 24(7): 1308-1313 (1996)). A corresponding PNA oligomer is prepared by chlorinating pyrimidine-5-acetic acid to yield 2-chloro-pyrimidine-5-acetic acid, 4-chloro-pyrimidine-5-acetic acid, and 2,4-dichloro-pyrimidine-5-acetic acid. Separation of isomers, followed by high temperature and pressure treatment with ammonia, gives the three corresponding amino-pyrimidine derivatives (see FIG. 9). The amino-pyrimidine derivatives are separated and amino-protected, then coupled to a protected PNA backbone ester. Ester hydrolysis results in PNA monomers for production of PNA oligomers containing 2-amino; 4-amino; and/or 2,4-diamino pyrimidine-5-yl bases.

3. Hydrolyzing the ethyl ester.
4. HBTU or Carbodiimide-mediated coupling of the nucleobase-acids to 2-Boc-aminoethyl-ethylglycinate.
5. Hydrolyzing the resulting monomer ester to the monomer free acid.
6. The resulting monomers may be used in Merrifield solid phase synthesis of xanthine, 2-thio-xanthine and 6-thio-xanthine-containing PNAs.

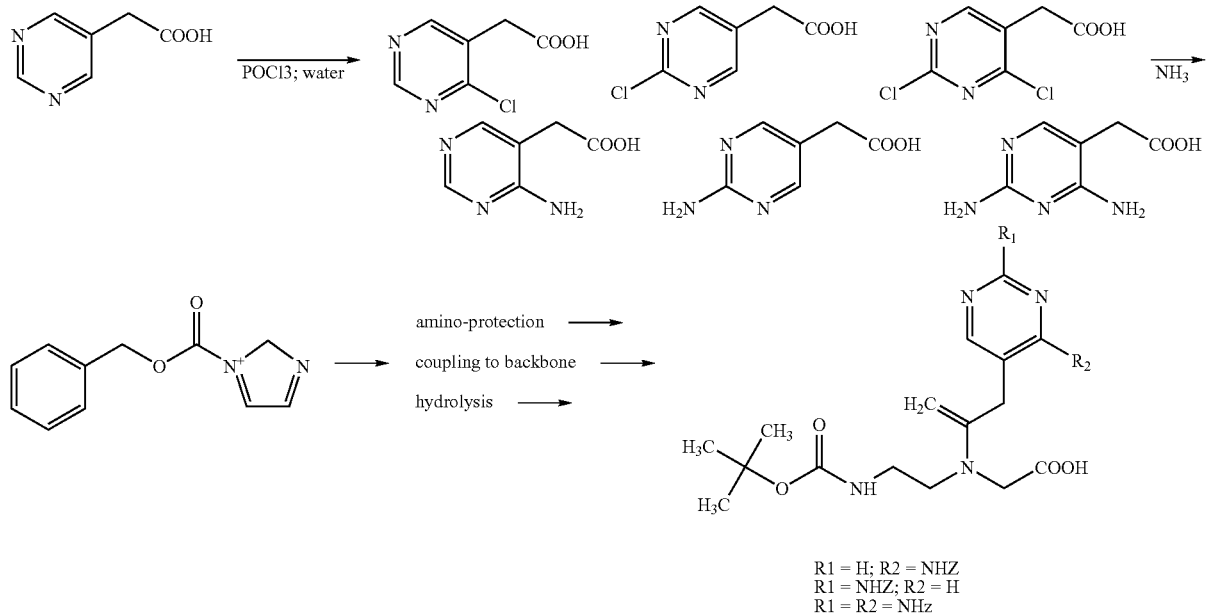

Example 17

Synthesis of Xanthine and Thio-Xanthine-Coupled PNA Monomers

Xanthine, 2-thio-xanthine, and 6-thio-xanthine are commercially available, for instance, from ScienceLab.com. Further, S. A. Benner et al., *Nucleic Acid Research* 24(7): 1308-1313 (1996) teaches the preparation of a xanthosine-DNA monomer, including a less acidic and preferable 7-deaza analog, and notes the preferred protection of both oxygens during solid phase synthesis.

Xanthine PNA-monomers, as well as 2-thio and 6-thio xanthine monomers, are prepared by:

1. Protecting both oxygens or both oxygen and sulphur with appropriate protection groups such as (possibly substituted) benzyl.
2. Alkylating at N-9 with ethyl bromacetate. (Separating N-7 alkylated byproduct.)

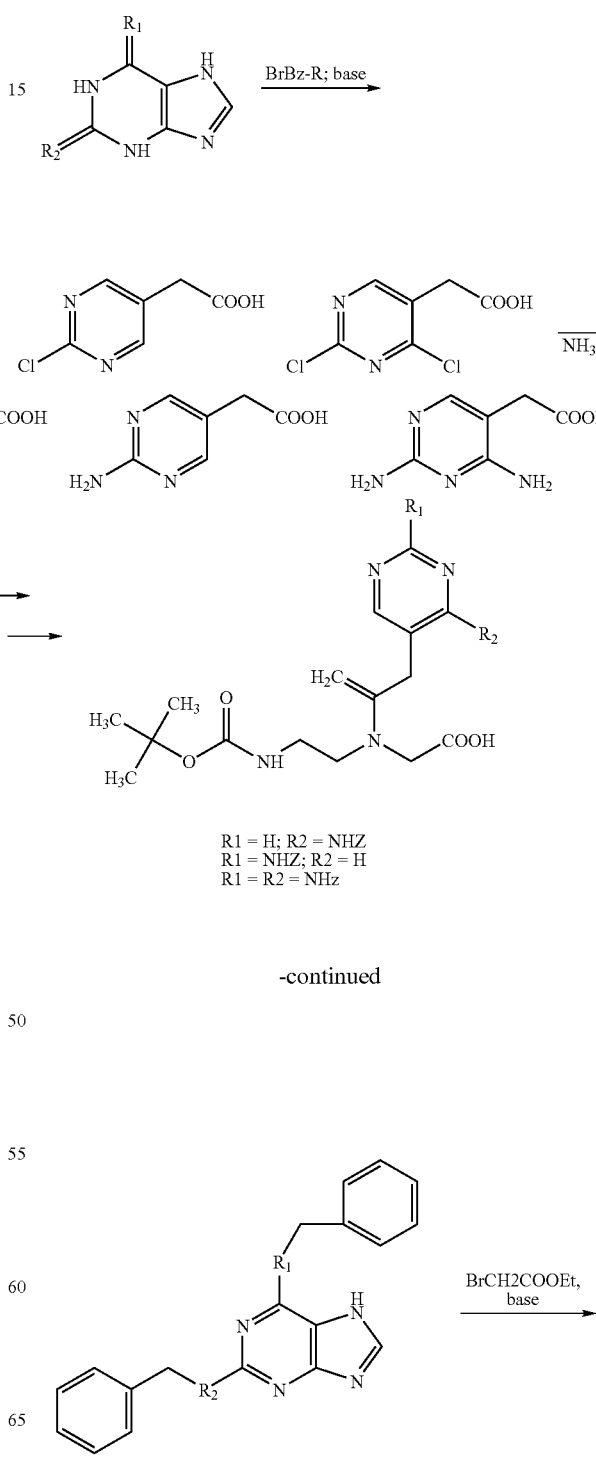

-continued

-continued

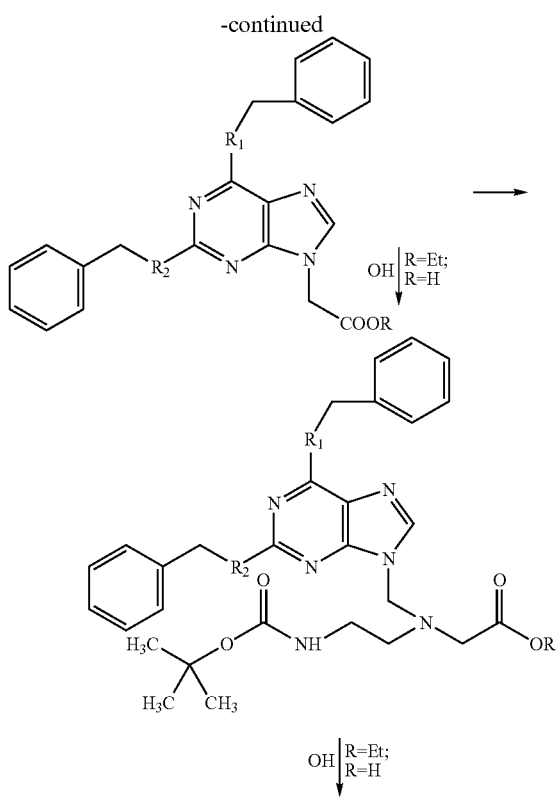

R1 = O; R2 = O
R1 = S; R2 = O
R1 = O; R2 = S

Example 18

Use of Specific IHC Detection Units with Different Linker Length

Aim:

To use 2-layer detection with horse radish peroxidase (HRP) to test and compare recognition units with different linker length (L150, L300, L540).

| Unit No. | Linker length | Specific score | Background score |
|---|---|---|---|
| 209-033 | L150 | 2.5+ | 1+ |
| 209-029 | L300 | 2.5+ | 1+ |
| 195-147 | L540 | 2+ | 0 |

Experimental Steps:

Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA1 (goat-anti-mouse-dextran-PNA1) (209-033, 209-029, or 195-147) was diluted to a final concentration of 0.08□M/dex in BP-HEPES-buffer (1.5% BSA, 3% PEG, 0.15M NaCl, 10 mM HEPES, pH 7.2) and was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA2-dex-HRP (209-041) was diluted to final concentration of 0.05□M/dex in BAP-HEPES-buffer (1.5% BSA, 3% PEG, 0.15M NaCl, 0.05% 4-aminoantipyrin, 10 mM HEPES, pH 7.2) and was applied. Following 10 minutes incubation at RT the sections were washed 5 minutes using 10× diluted S3006 (Dako).

Prepared DAB+ working solution (an aqueous imidazole buffer with hydrogen peroxide and DAB; K3468 Dako) was applied. Following 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result:

The brown end product of the HRP reaction visualize the specific cytokeratin staining of epithelia cells and show no significant difference in performance when comparing recognition units having different linker length.

Example 19

IHC Testing of Detection Units with Different Number of Linker-PNA Attached

Aim:

to use 2-layer HRP detection to test and compare detection units with different number of PNA per dextran (0.8 PNA/dex and 1.5 PNA/dex).

| Unit No. | PNA/dex | Specific score | Background score |
|---|---|---|---|
| 195-051 | 0.8 | 3+ | 0.5+ |
| D15008 | 1.5 | 3+ | 0.5+ |

Experimental Steps:

Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA1 (195-047) diluted to final concentration of 0.08□M/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA2-dex-HRP (HRP=horse radish peroxidase) (195-051 or D15008) diluted to final concentration of 0.05□M/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result:

The brown end product of the HRP reaction visualize the specific cytokeratin staining of epithelia cells and show no significant difference in performance when comparing detection units having different number of PNA/dex.

Example 20

IHC Testing Comparing Recognition and Detection Units Having "Linker-PNA" or "Linker-PNA-Linker Tail" Attached Aim:

To use 2-layer detection to test and compare recognition and detection units having PNA sequences without and with "linker tail".

| Unit No. GaM-dex-PNA | tail | Unit No. PNA-dex-HRP | tail | Specific score | Background score |
|---|---|---|---|---|---|
| 218-113 | No | 218-021 | No | 3+ | 1+ |
| D16074 | Yes | 218-021 | No | 3+ | 0.5+ |
| 218-113 | No | D16076 | Yes | 3+ | 0.5+ |
| D16074 | Yes | D16076 | Yes | 4+ | 1.5+ |

Experimental Steps:

Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako). GaM-dex-PNA (218-113 or D16074) diluted to final concentration of 0.08 $\square$M/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA-dex-HRP (218-021 or D16076) diluted to final concentration of 0.05 $\square$M/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result:

The brown end product of the HRP reaction visualize the specific cytokeratin staining of epithelia cells and show that performance depend on the presence of a "linker tail" on the PNA sequence. A "linker-tail" on the PNA sequence may influence both specific score and background score.

Example 21

IHC Testing Comparing Recognition and Detection Units Having "Linker-PNA" or "Linker-PNA-Charge" Attached Aim:

to use 2-layer HRP detection to test and compare recognition and detection units having PNA sequences without and with charge.

| Unit No. GaM-dex-PNA | charge | Unit No. PNA-dex-HRP | charge | Specific score | Background score |
|---|---|---|---|---|---|
| D15078 | No | D15069 | No | 0.5+ | 0 |
| 209-149 | Yes | 209-157 | Yes | 3+ | 1+ |

Experimental Steps:

Primary mouse antibody M3515 (Dako) targeting CK was diluted to final 1:200 in S2022 (Dako) and applied on a multi tissue section. Following 10 minutes incubation at RT the section was washed 5 minutes using 10× diluted S3006 (Dako).

GaM-dex-PNA (D15078 or 209-149) diluted to final concentration of 0.08 $\square$M/dex in BP-HEPES-buffer (1.5% BSA, 3% PEG, 0.15M NaCl, 10 mM HEPES, pH 7.2) was applied. Following 10 minutes incubation at RT the section was washed 5 minutes using 10× diluted S3006 (Dako). The sections were rinsed in deionized water. Following 10 minutes incubation in 0.5% glutaraldehyde at RT the sections were rinsed in deionized water and washed 5 minutes using 10× diluted S3006 (Dako).

PNA-dex-HRP (D15069 or 209-157) diluted to final concentration of 0.05 $\square$M/dex in BAP-HEPES-buffer (1.5% BSA, 3% PEG, 0.15M NaCl, 0.05% 4-aminoantipyrin, 10 mM HEPES, pH 7.2) was applied. Following 10 minutes incubation at RT the sections were washed 5 minutes using 10× diluted S3006 (Dako).

Prepared DAB+ working solution (Dako K3468) was applied. Following. 10 minutes incubation the sections were washed 5 minutes deionized water. Finally the sections were counter stained 5 minutes using haematoxylin S3301 (Dako), rinsed in deionized water, washed 3 minutes in wash buffer, and mounted in Faramount S3025 (Dako).

Result:

The brown end product of the HRP reaction visualize the specific cytokeratin staining of epithelia cells and show that performance depend on the presence of charge on the PNA sequence. Charge on the PNA sequences within a PNA pair may influence both specific score and background score.

Example 22

Synthesis and IHC Testing of an Antibody-PNA Conjugate

Part A. Testing Different Ratios of Linker to Antibody.

Materials:

Antibody: CD 45 dialyzed overnight against 0.01 M Hepes 0.1 M NaCl pH=7.2. SMCC: Succinimidyl-4(N-maleimidomethyl)cyclohexan-1-carboxylate molw. 334.33. PNA: Acetyl-$L_{30}$-GTP-TAA-TTP-PAG-$L_{150}$-Lys(Cys)

Test 1

10 nmol CD45 was dissolved in 161 µL 0.01 M Hepes 0.1 M NaCl pH=7.2. 250 nmol SMCC was dissolved in 8 µL NMP. The above components were mixed and placed in a water bath at 30° C. for 60 minutes. The mixture was purified on a mini-prep column (Sephadex G-25) with 0.01 M Hepes 0.1 M NaCl pH=7.2 as eluent. Fractions of 0.3 mL. By measuring absorbance at 278 nm three fractions containing the product (58%) were identified. These three fractions were added to 100 nmol of a lyophilized PNA. Then 1 µL 5% Di-Sodium-EDTA/water was added and the solution was mixed until dissolved and placed in a water bath at 30° C. for 30 minutes. Quenching was performed by adding 2 mg of Cysteine. Water bath 30° C. for 30 minutes.

The product was purified on FPLC: Column SUPERDEX®-75, Buffer 0.01 M Hepes 0.1 M NaCl pH 7.2. The fraction with the product was collected. Relative absorbance between PNA ($\epsilon_{260\ nm}$) and antibody ($\epsilon_{278}$ nm) was used to calculate the average conjugation ratio of PNA and antibody. PNA/CD45: 5.2. Yield 39% based on antibody.

Test 2

10 nmol CD45 was dissolved in 161 µL 0.01 M Hepes 0.1 M NaCl pH=7.2. 150 nmol SMCC was dissolved in 5 µL NMP. The above components were mixed and placed in a water bath at 30° C. for 60 minutes. The mixture was purified on a mini-prep column (SEPHADEX® G-25) with 0.01 M Hepes 0.1 M NaCl pH=7.2 as eluent. Fractions of 0.3 mL. By measuring absorbance at 278 nm three fractions containing the product (74%) were identified.

These three fractions were added to 100 nmol of a lyophilized PNA. Then 1 µL 5% Di-Sodium-EDTA/water was added and the solution was mixed until dissolved and placed in a water bath at 30° C. for 30 minutes. Quenching was performed by adding 2 mg of cysteine. Water bath 30° C. for 30 minutes.

The product was purified on FPLC: Column Superdex-75, Buffer 0.01 M Hepes 0.1 M NaCl pH 7.2. The fraction with the product was collected. Relative absorbance between PNA ($\epsilon_{260\ nm}$) and antibody ($\epsilon_{278\ nm}$) was used to calculate the average conjugation ratio of PNA and antibody. PNA/CD45: 3.4. Yield 55% based on antibody.

IHC Test of Conjugates

A later IHC test showed that PNA/CD45 in Test 2 gave a higher score than the one in Test 1. This brought us to the conclusion that the ratio between CD45/SMCC/PNA should be 10/150/100.

Part B. Test of Different Conjugation Times—Antibody and Linker

Materials:

Antibody: GAM (goat-anti-mouse) dialyzed overnight against 0.1 M NaCl. SMCC: Succinimidyl-4(N-maleimidomethyl)cyclohexan-1-carboxylate molw. 334.33. Flu-Link: Flu-$L_{90}$-Lys(Flu)-$L_{30}$-Lys(Cys)

Test 1

20 nmol GAM was dissolved in 402 µL 0.01 M Hepes 0.1 M NaCl pH=7.2. 400 nmol SMCC dissolved in 13 µL NMP. The above components were mixed and placed in a water bath at 30° C. for 1 hour. 207 µL of the mixture was purified on a mini-prep column (SEPHADEX® G-25) with 0.01 M Hepes 0.1 M NaCl pH=7.2 as eluent. Fractions of 0.3 mL were taken. By measuring absorbance at 278 nm, three fractions containing the product (79%) were identified. These three fractions were added to 200 nmol of a lyophilized Flu-Link. Then 1 µL 5% di-sodium-EDTA/water was added and the solution was mixed until dissolved and placed in a water bath at 30° C. overnight. Quenching was performed by adding 2 mg of Cysteine. Water bath 30° C. for 30 minutes.

The product was purified on FPLC: Column SUPERDEX®-75, Buffer 0.01 M Hepes 0.1 M NaCl pH 7.2. The fraction with the product was collected. Relative absorbance between Flu-Link ($\epsilon_{498\ nm}$) and antibody ($\epsilon_{278\ nm}$) was used to calculate the average conjugation ratio of PNA and antibody. Flu-Link/GAM: 7.1. Yield 55% based on antibody.

Test 2

20 nmol GAM was diluted with 402 µL 0.01 M Hepes 0.1 M NaCl pH=7.2. 400 nmol SMCC was dissolved in 13 µL NMP. The above components were mixed and placed in a water bath at 30° C. for 2 hours. The rest of the synthesis and purification was done in exactly the same procedure as for 1 hour. There was a 64% yield of GAM/SMCC before adding the Flu-Link. Flu-Link/GAM: 8.7. Yield 33% based on antibody.

Part C. Test of Different Conjugation Times—Fluorophore and Linker

Materials:

Antibody: GAM dialyzed overnight against 0.1 M NaCl. SMCC: Succinimidyl-4(N-maleimidomethyl)cyclohexan-1-carboxylate molw. 334.33. Flu-Link: Flu-$L_{90}$-Lys(Flu)-$L_{30}$-Lys(Cys)

Test 1

20 nmol GAM was dissolved 378 µL 0.01 M Hepes 0.1 M NaCl pH=7.2. 400 nmol SMCC was dissolved in 13 µL NMP. The above components were mixed and placed in a water bath at 30° C. for 1 hour. The mixture was divided in two and purified on two mini-prep columns (SEPHADEX® G-25) with 0.01 M Hepes 0.1 M NaCl pH=7.2 as eluent. Fractions of 0.3 mL were taken. By measuring absorbance at 278 nm, three fractions from each column containing the product (76% in all) were identified. These six fractions were pooled, divided in two, and each added to 200 nmol of a lyophilized Flu-Link. Then 1 µL 5% di-sodium-EDTA/water was added and the solution was mixed until dissolved and placed in a water bath at 30° C., one for 30 minutes, the other for 60 minutes. Quenching was performed by adding 2 mg of cysteine. Water bath 30° C. for 30 minutes.

The product was purified on FPLC: Column SUPERDEX®-75, Buffer 0.01 M Hepes 0.1 M NaCl pH 7.2. The fractions with the product from each purification were collected. Relative absorbance between Flu-Link ($\epsilon_{498\ nm}$) and antibody ($\epsilon_{278\ nm}$) was used to calculate the average conjugation ratio of PNA and antibody. 30 minutes conjugation Flu-Link/GAM: 7.0 Yield 55% based on antibody. 60 minutes conjugation Flu-Link/GAM: 6.9 Yield 52% based on antibody. The above results show that 30 minutes conjugation between GAM/SMCC and Flu-Link is sufficient.

Other exemplary embodiments include linker derivatives of one of the following structures:

a. Lys($PNA_1$)-L30-$PNA_2$-L30-Lys($PNA_1$)-L30-Lys($PNA_1$)-L30-Lys($PNA_1$)
b. $PNA_1$-linker-($PNA_1$-linker)$_n$-$PNA_1$-linker-$PNA_2$
c. $PNA_1$-linker-($PNA_1$-linker)$_n$-$PNA_1$-linker-$PNA_2$-linker-$PNA_1$-linker-($PNA_1$-linker)$_n$-$PNA_1$
d. $PNA_1$-linker-(Lys(linker-$PNA_1$)-linker)$_n$-Lys(linker-$PNA_1$)-linker-$PNA_2$
e. $PNA_1$-linker-(Lys(linker-$PNA_1$)-linker)$_n$-linker-$PNA_2$-(linker-Lys(linker-$PNA_1$))$_n$.

Other examples include linker derivatives of the general structure: $([L15]_n\text{-}PNA)_m$, in which the linker derivative is further coupled covalently or non-covalently to an antibody and/or to dextran, and in which n and m are integers greater than or equal to 1.

Yet other examples include linker derivatives of the general structure: $([L15]_n\text{-}F)_m$, in which the linker derivative is further attached covalently or non-covalently to an antibody and/or to dextran, and in which F is a fluorophore and n and m are integers greater than or equal to 1.

Yet other examples include:

Fluorescent microspheres comprising linkers conjugated to lissamine, and/or to color labels such as DNP or fluorescent dyes such as fluorescein or rhodamine or their derivatives, and/or to PNA.

Systems such as: antibody:dextran:(L-PNA)$_n$; antibody:dextran:(L-F)$_n$; PNA-L:dextran:(L-F)$_n$; PNA-L:dextran:(HRP enzyme); $PNA_1$-L:dextran-(L-$PNA_2$)$_n$; in which L represents a linker of at least one L-15 unit, F represents a fluorophore, n represents an integer of greater than or equal to 1, ":" represents a covalent or non-covalent attachment, and "-" represents a covalent attachment.

Additional applications of the instant linkers are described in U.S. Provisional Patent Application Nos. 60/695,408; 60/695,409; and 60/695,410; and International Patent Applications entitled "New Nucleic Acid Base Pairs" and "Method of Detecting a Target in a Sample," the entire disclosures of which are incorporated herein by reference.

Yet other embodiments of the invention will be apparent to those skilled in the art from consideration of the specification and practice of the invention disclosed herein. It is intended that the specification and examples be considered as exemplary only, with a true scope and spirit of the invention being indicated by the claims.

What is claimed is:

1. A linker comprising at least two consecutive units chosen from:

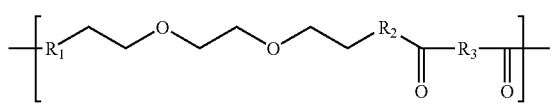

Formula I wherein $R_1$ is chosen from NH and O, $R_2$ is chosen from NH and O, and $R_3$ is chosen from methyl, ethyl, propyl, $CH_2OCH_2$ and $(CH_2OCH_2)_2$, and wherein the linker does not comprise more than three consecutively repeating ethyloxy groups.

2. The linker of claim 1, comprising at least one unit of Formula I in which $R_1$ and $R_2$ are NH and $R_3$ is $CH_2OCH_2$.

3. The linker of claim 1, comprising between three and ten consecutive units of the structure of Formula I.

4. A method of enhancing the signal intensity, activity, or binding affinity of a molecule, comprising conjugating the molecule to a linker comprising at least two consecutive units chosen from:

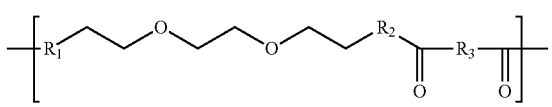

Formula I wherein $R_1$ is chosen from NH and O, $R_2$ is chosen from NH and O, and $R_3$ is chosen from methyl, ethyl, propyl, $CH_2OCH_2$, and $(CH_2OCH_2)_2$, and wherein the resulting conjugate of the molecule and linker does not comprise more than three consecutively repeating ethyloxy groups.

5. The method of claim 4, wherein the linker comprises at least one unit of the Formula I wherein $R_1$ and $R_2$ are NH and R3 is $CH_2OCH_2$.

6. The method of claim 4, wherein the linker comprises between three and ten consecutive units of Formula I.

7. The method of claim 4, wherein the molecule comprises at least one detectable label or probe.

8. The method of claim 7, wherein the molecule comprises at least one detectable label and wherein the at least one detectable label comprises at least one color label.

9. The method of claim 8, wherein the at least one color label comprises a fluorophore.

10. The method of claim 9, wherein molecule comprises at least one nucleic acid or nucleic acid analog.

11. The method of claim 10, wherein the at least one nucleic acid analog comprises PNA.

12. The method of claim 4, wherein the aqueous solubility of the molecule is enhanced over its solubility in the absence of the linker.

13. A system comprising at least two linker derivatives, wherein the linker comprises at least two consecutive units chosen from:

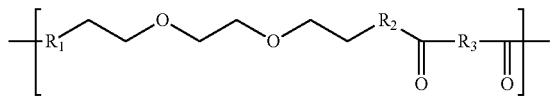

Formula I wherein $R_1$ is chosen from NH and O, $R_2$ is chosen from NH and O, and $R_3$ is chosen from methyl, ethyl, propyl, $CH_2OCH_2$ and $(CH_2OCH_2)_2$, and wherein the linker derivatives do not comprise more than three consecutively repeating ethyloxy groups, and wherein the first linker derivative comprises at least one fluorophore and a nucleic acid or nucleic acid analog; and wherein the second linker derivative comprises a protein or solid surface and a nucleic acid or nucleic acid analog.

14. The system of claim 13, wherein the nucleic acid analog is PNA.

15. The system of claim 13, wherein nucleic acid or nucleic acid analogs of the first and second linker derivatives are capable of hybridizing to each other.

16. The system of claim 13, wherein the first linker derivative is conjugated to at least one fluorophore and to a PNA; and wherein protein or solid surface of the second linker derivative is an antibody, an antigen, and/or dextran; and wherein the PNA of the first linker and second linker derivatives are capable of hybridizing to each other.

17. The system of claim 13, comprising three linker derivatives.

18. The system of claim 14, comprising three linker derivatives.

19. The system of claim 14, wherein the first and second linker derivatives are not capable of hybridizing to each other, and wherein the third linker derivative comprises at least one PNA that recognizes PNA sequences on each of the first and second linker derivatives.

* * * * *